United States Patent
Ramanathan et al.

(10) Patent No.: US 8,849,389 B2
(45) Date of Patent: *Sep. 30, 2014

(54) VISUALIZATION OF ELECTROPHYSIOLOGY DATA

(71) Applicant: Cardioinsight Technologies, Inc., Cleveland, OH (US)

(72) Inventors: Charulatha Ramanathan, Solon, OH (US); Harold M. Wodlinger, Thornhill (CA); Harris Gasparakis, Lexington, MA (US); Steven G. Arless, Baie Durfe (CA); John E. Anderson, Chagrin Falls, OH (US); Soniya Bhojwani, Cleveland, OH (US)

(73) Assignee: Cardioinsight Technologies, Inc., Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/932,523

(22) Filed: Jul. 1, 2013

(65) Prior Publication Data

US 2014/0005563 A1 Jan. 2, 2014

Related U.S. Application Data

(63) Continuation of application No. 13/128,123, filed as application No. PCT/US2009/063937 on Nov. 10, 2009, now Pat. No. 8,478,393.

(60) Provisional application No. 61/112,961, filed on Nov. 10, 2008.

(51) Int. Cl.
A61B 5/044 (2006.01)
A61B 5/04 (2006.01)
A61B 5/00 (2006.01)

(52) U.S. Cl.
CPC ............ *A61B 5/044* (2013.01); *A61B 5/726* (2013.01); *A61B 5/04012* (2013.01)
USPC ..................... 600/523; 600/509; 600/508

(58) Field of Classification Search
CPC ..... A61B 5/044; A61B 5/0432; A61B 5/0452; A61B 5/0006
USPC .......................... 600/508, 509, 523
See application file for complete search history.

(56) References Cited

U.S. PATENT DOCUMENTS 3,954,098 A 5/1976 Dick et al.
4,974,598 A 12/1990 John (Continued)

OTHER PUBLICATIONS

Wang, et al., "Application of the Method of Fundamental Solutions to Potential-based Inverse Electrocardiography", Annals of Biomedical Engineering, vol. 34, No. 8, Aug. 2006 (2006 ©), pp. 1272-1288.

(Continued)

*Primary Examiner* — Christopher D Koharski
*Assistant Examiner* — Michael Carey
(74) *Attorney, Agent, or Firm* — Tarolli, Sundheim, Covell & Tummino LLP

(57) ABSTRACT

A method for visualization of electrophysiology information can include storing electroanatomic data in memory, the electroanatomic data representing electrical activity on an anatomic region within a patient's body over a time period. An interval within the time period is selected in response to a user selection. A visual representation of physiological information for the user selected interval can be generated by applying at least one analysis method to the electroanatomic data. The visual representation can spatially represented on a graphical representation of the anatomic region within the patient's body.

20 Claims, 15 Drawing Sheets

(56) References Cited

U.S. PATENT DOCUMENTS

| | | | |
|---|---|---|---|
| 5,038,791 | A | 8/1991 | Collins et al. |
| 5,054,496 | A | 10/1991 | Wen et al. |
| 5,161,539 | A | 11/1992 | Evans et al. |
| 5,390,110 | A | 2/1995 | Cheney et al. |
| 5,480,422 | A | 1/1996 | Ben-Haim |
| 5,687,737 | A | 11/1997 | Branham et al. |
| 5,692,515 | A | 12/1997 | Rahn et al. |
| 5,697,377 | A | 12/1997 | Wittkampf |
| 5,713,946 | A | 2/1998 | Ben-Haim |
| 5,738,096 | A | 4/1998 | Ben-Haim |
| 5,803,084 | A | 9/1998 | Olson |
| 5,848,972 | A | 12/1998 | Triedman et al. |
| 5,891,049 | A | 4/1999 | Cyrus et al. |
| 6,016,439 | A | 1/2000 | Acker |
| 6,368,285 | B1 | 4/2002 | Osadchy et al. |
| 6,650,927 | B1 | 11/2003 | Keidar |
| 6,782,287 | B2 | 8/2004 | Grzeszczuk et al. |
| 6,788,969 | B2 | 9/2004 | Dupree et al. |
| 6,920,350 | B2 | 7/2005 | Xue et al. |
| 7,016,719 | B2 | 3/2006 | Rudy et al. |
| 7,189,208 | B1 | 3/2007 | Beatty et al. |
| 7,266,408 | B2 | 9/2007 | Bojovic et al. |
| 7,286,866 | B2 | 10/2007 | Okerlund et al. |
| 8,478,393 | B2 * | 7/2013 | Ramanathan et al. ........ 600/523 |
| 2004/0006268 | A1 | 1/2004 | Gilboa et al. |
| 2005/0070781 | A1 | 3/2005 | Dawant et al. |
| 2006/0116575 | A1 | 6/2006 | Willis |
| 2007/0073179 | A1 * | 3/2007 | Afonso et al. ................ 600/523 |
| 2007/0208260 | A1 * | 9/2007 | Afonso ........................ 600/508 |
| 2007/0299351 | A1 | 12/2007 | Harlev et al. |
| 2008/0009758 | A1 | 1/2008 | Voth |
| 2008/0188765 | A1 * | 8/2008 | Stolarski et al. .............. 600/518 |
| 2008/0249424 | A1 | 10/2008 | Harlev et al. |

OTHER PUBLICATIONS

Burnes, et al., "A Field-Compatible Method for Interpolating Biopotentials", Annals of Biomedical Engineering, vol. 26, 1998, pp. 37-47.

Jia, et al., "Endocardial Mapping of Electrophysiologically Abnormal Substrates and Cardiac Arryhthmias Using a Noncontact Nonexpandable Catheter", Journal of Cardiovascular Electrophysiology, vol. 13, No. 9, Sep. 2002, Copyright © 2002 by Future Publishing Company, Inc., pp. 888-895.

Khoury, et al., "A Model Study of Volume Conductor Effects on Endocardial and Intracavitary Potentials", Department of Biomedical Engineering, Case Western Reserve University, Apr. 17, 1992, pp. 511-525.

* cited by examiner

VISUALIZATION OF ELECTROPHYSIOLOGY DATA

CROSS-REFERENCE TO RELATED APPLICATIONS

This application is a continuation of U.S. patent application Ser. No. 13/128,123(Now U.S. Pat. No. 8,478,393), filed Aug. 22, 2011, entitled VISUALIZATION OF ELECTROPHYSIOLOGY DATA, which is a U.S. national stage entry under 35 U.S.C. 371 of International Application No. PCT/US2009/063937, which claims the benefit of U.S. Provisional Patent Application No. 61/112,961, which was filed on Nov. 10, 2008, and entitled ANALYSIS OF CARDIAC ELECTRICAL ACTIVITY AND ASSOCIATED WORKFLOWS, the entire contents of which applications are incorporated herein by reference. This application is also related to International Application No. PCT/US09/63737, entitled VISUALIZATION OF PHYSIOLOGICAL DATA FOR VIRTUAL ELECTRODES and filed Nov. 9, 2009, which is also incorporated herein by reference.

TECHNICAL FIELD

The invention relates generally to visualization of electrical activity of a patient, and more particularly to spatial visualization of electrophysiology data for a patient.

BACKGROUND

Electrophysiology data is used in the diagnosis and treatment of cardiac arrhythmias. Electrophysiology data can be gathered and displayed in various ways, including with the use of electrophysiology catheters (both contact and non-contact), patches or other devices containing electrodes placed in contact with the surface of the heart, or reconstruction using electrocardiographic or other means.

Electrophysiology data is used in the diagnosis and treatment of cardiac arrhythmias. Electrophysiology data can be displayed in the form of electroanatomic maps, which spatially depict electrophysiology data on a representation of an organ or a body surface; however, electrophysiology data is used by clinicians treating arrhythmias both in the form of electroanatomic maps and also in other ways, for example by analyzing electrophysiology data generated at certain points.

During complex arrhythmias, cardiac electrical activity can be extremely complex and difficult to analyze and/or interpret using standard signal processing techniques. An example of a complex arrhythmia is atrial fibrillation (or "Afib"), which can involve fast and irregular electrical activity resulting in complex electrograms.

SUMMARY

The invention relates generally to visualization of electrical activity, and more particularly to spatial visualization of electrophysiology data for a patient.

One aspect of the invention provides a method for visualization of electrophysiology information. The method includes storing electroanatomic data in memory, the electroanatomic data representing electrical activity on a surface of an organ over a time period. An interval is selected within the time period in response to a user selection. Responsive to the user selection of the interval, a visual representation of physiological information is generated for the user selected interval by applying at least one method to the electroanatomic data. The visual representation can be spatially represented on a graphical representation of a predetermined region of the surface of the organ.

The at least one method can, for example, include preprocessing the signals to be substantially optimal for advanced analysis, detecting local activations in a given signal, delineating the cycle length, extracting frequencies of highest dominance and regularity, and identifying anatomic regions sustaining culprit circuits and other regions of abnormal cellular properties (e.g., for repolarization) relevant to the arrhythmia. This information can be visualized in a site-specific manner or presented as electroanatomic maps, which may be static or include animations. Statistical and visualization techniques to compare various processing outputs can also be implemented.

The systems and methods are equally applicable to analyzing cardiac electrical potentials measured directly via catheter mapping during an electrophysiology study, using an electrode patch during open heart surgery, or reconstructed using electrocardiographic imaging or other means.

DETAILED DESCRIPTION

Figure 1:
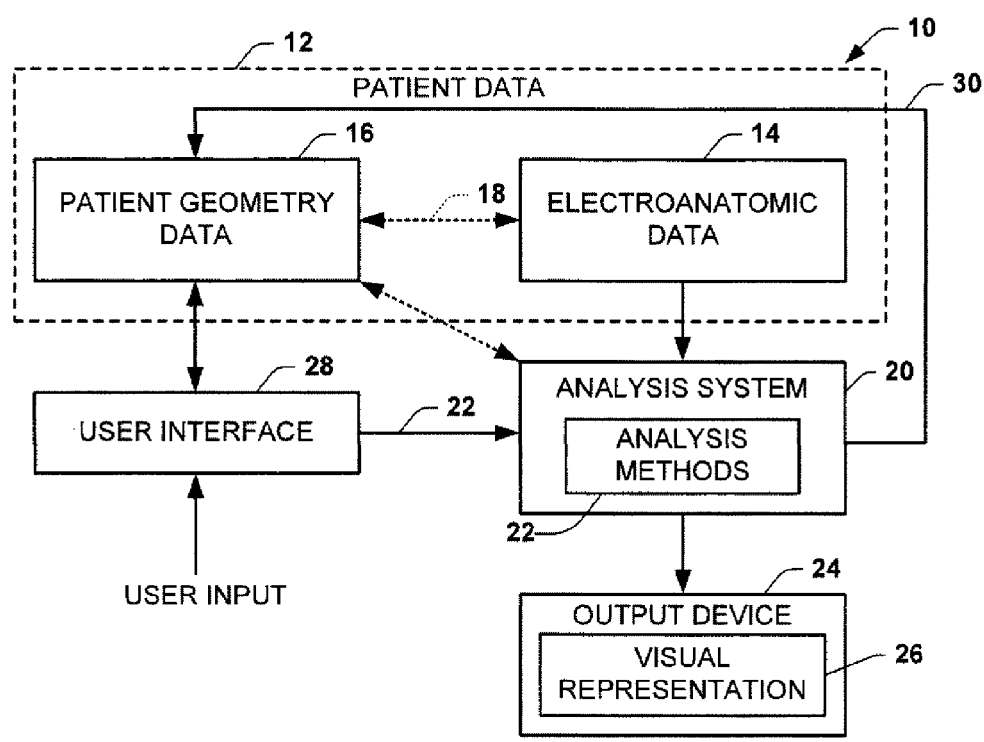
FIG. 1 depicts a block diagram of a system for visualizing physiological data in accordance with an aspect of the invention.

The invention relates generally to visualization of electrical activity of a patient, and more particularly to spatial visualization of electrophysiology data for a patient.

In one embodiment, electroanatomic data can be stored in memory to represent electroanatomic data for electrical activity on a surface of an organ over a time period. Tools are provided to allow a user to select an interval within the time period. Responsive to the user selection of the interval, a visual representation of physiological information is generated for the user selected interval by applying at least one method to the electroanatomic data. Various methods can be used to provide respective spatial visualizations of desired physiological information. For instance, the visual representation can be spatially represented (e.g., as an electroanatomic map) on a graphical representation of a predetermined region of the surface of the organ. As a further example, one or more virtual electrodes can be positioned on a point on the organ surface to provide a corresponding electrogram or a plot of other physiological information for the electrode(s). Thus, a user can utilize spatially relevant information gleaned from the electrogram or a plot of other physiological information to guide selection of the interval. The user can further vary the interval to dynamically change the resulting visual representation.

As used herein, the term "virtual" in the context of electrodes or other selected anatomical locations means that the selected location or structure is not a physical electrode construction, but instead is parameterized by data (e.g., as mathematical model) at a point, a collection of points or a substantially continuous surface region that is selected by a user. The resulting visual representation of the physiological data for a given virtual electrode thus can represent electrophysiology data that has been acquired, that has been computed or a combination of acquired and computed data for a set of one or more geometrical points associated with a surface region of the patient.

Those skilled in the art will appreciate that portions of the invention may be embodied as a method, data processing system, or computer program product. Accordingly, these portions of the invention may take the form of an entirely hardware embodiment, an entirely software embodiment, or an embodiment combining software and hardware. Furthermore, portions of the invention may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments of the invention are described herein with reference to flowchart illustrations of methods, systems, and computer program products. It will be understood that blocks of the illustrations, and combinations of blocks in the illustrations, can be implemented by computer-executable instructions. These computer-executable instructions may be provided to one or more processors of a general purpose computer, special purpose computer, or other programmable data processing apparatus (or a combination of devices and circuits) to produce a machine, such that the instructions, which execute via the processor, implement the functions specified in the block or blocks.

Figure 17:
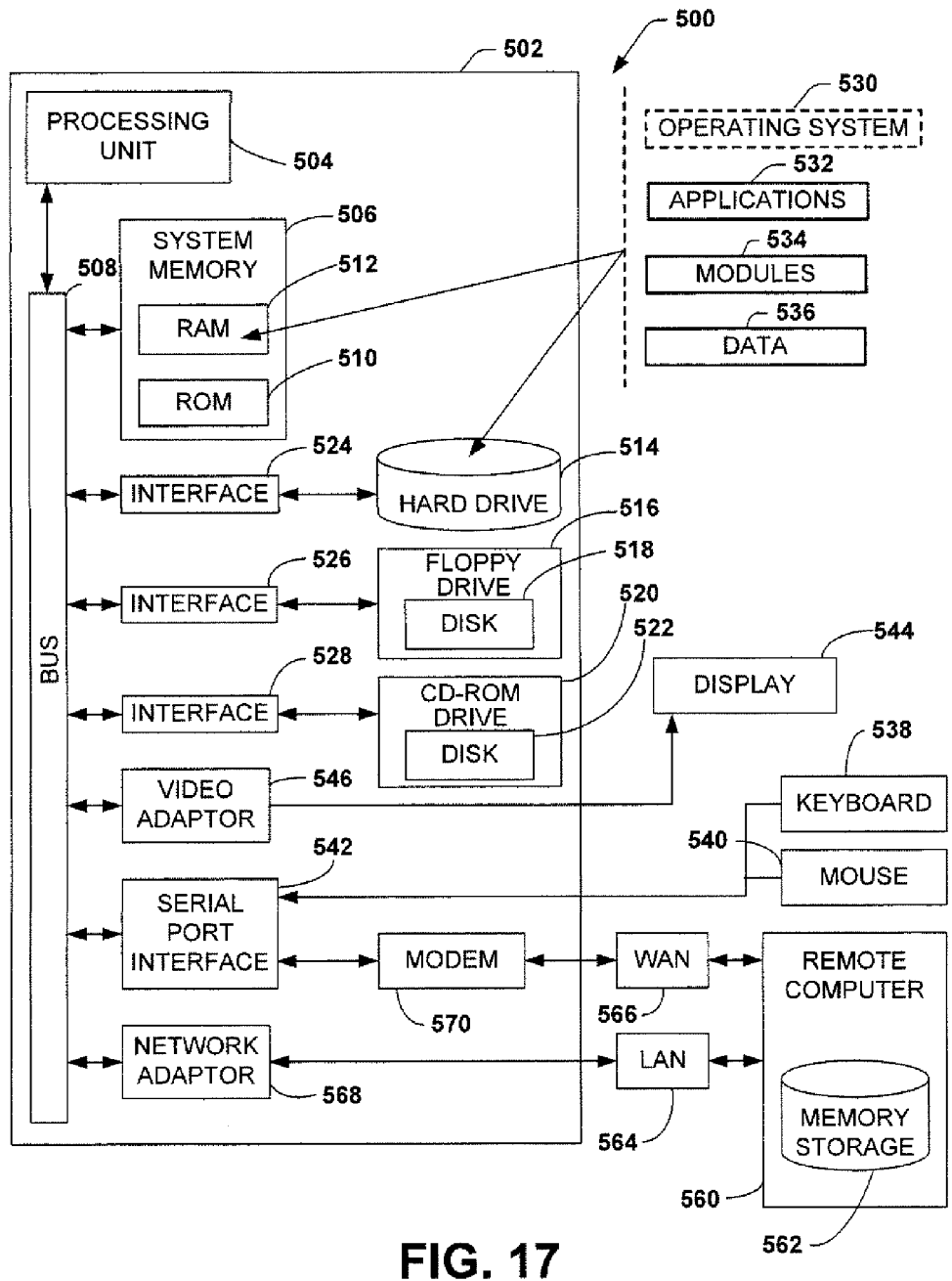
FIG. 17 depicts an example computing environment that can be used in performing methods and processing according to an aspect of the invention.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus (see, e.g., FIG. 17) to cause a series of operational steps to be performed on the computer or other programmable apparatus to produce a computer implemented process such that the instructions which execute on the computer or other programmable apparatus provide steps for implementing the functions specified in the flowchart block or blocks.

FIG. 1 depicts an example of a system 10 for visualizing physiological data of a patient. The system 10 can be implemented in a standalone computer, a workstation, an application specific machine, or in a network environment in which one or more of the modules or data can reside locally or remotely relative to where a user interacts with the system 10.

The system 10 includes patient data 12 for one or more patient, such as can be stored in an associated memory device (e.g., locally or remotely). The patient data 12 can include electroanatomic data 14 that represents electrical information for a plurality of points, each of which is indexed or otherwise associated with an anatomical geometry of the patient. The patient data 12 can also include patient geometry data 16, such as can be embodied as a patient geometry model. In one embodiment, the patient geometry data can correspond to a surface of model of a patient's entire organ, such as the heart, which can be graphically rendered as a two- or three-dimensional representation.

The patient electroanatomic data 14 can be raw data, such as has been collected from an electrophysiology mapping catheter or other means that can be utilized to gather electrophysiology data for a selected region of a patient (e.g., of an organ, such as the heart). Additionally or alternatively, the electroanatomic data 14 can correspond to processed data, such as can be computed from raw data to provide electrophysiology information for the selected region of the patient (e.g., a surface of an organ, such as the heart).

By way of example, a contact or non-contact electrophysiology catheter can be placed in a patient's heart and collect electrophysiology data at a plurality of spatial locations over time, such as during a number of one or more cardiac intervals. Such data can be spatially and temporarily aggregated in conjunction with image data for the patient's heart to provide the electroanatomic data 14 for the patient's heart. Alternatively, other devices (e.g., catheters or patches) can be placed on or near a patient's heart, endocardially and/or epicardially, such as during open chest and minimally invasive procedures, to record electrical activity data, which can be mapped to a representation of the patient's heart to provide similar corresponding electroanatomic data 14.

As another example, non-invasive electrophysiological mapping (e.g., electrocardiographic imaging for the heart) can be performed on the patient to generate the electroanatomic data 14. This technique can generate electrophysiological data by combining body surface electrical measurements with patient geometry information through an inverse method programmed to reconstruct the electrical activity for a predetermined surface region of the patient's organ. Thus the results of the inverse method can provide the corresponding electroanatomic data 14 that is registered with (or indexed) relative to patient geometry data 16.

Those skilled in the art will understand and appreciate that the system 10 is equally applicable to patient electroanatomic data 14 that can be gathered and/or derived by any of these or other approaches, which may be invasive or non-invasive. Additionally, it will be understood and appreciated that the electroanatomic data 14 can be provided in any form and converted into an appropriate form for processing in the system 10.

In addition to the patient electroanatomic data 14 related to the patient's organ, the system 10 also employs the patient geometry data 16, such as can represent a predetermined surface region of an anatomical structure of a patient. For example, the patient geometry data 16 can correspond to a patient-specific representation of a surface of an organ or other structure to which the patient electroanatomical data has been registered. For instance, the patient geometry data 16 may include a graphical representation of a region of the patient's organ, such as can be generated by appropriate imaging processing of image data acquired for the patient. Such image processing can include extraction and segmentation of an organ from a digital image set. The segmented image data thus can be converted into a two-dimensional or three-dimensional graphical representation of a surface region of the patient's organ. Alternatively, the patient geometry data 16 can correspond to a mathematical model of the patient's organ that has been constructed based on image data for the patient's organ. Appropriate anatomical or other landmarks can be associated with the organ represented by the anatomical data for the organ to facilitate subsequent processing and visualization in the system 10.

As mentioned above, the electroanatomic data 14 can be registered into a common coordinate system with the patient geometry data 16. For instance, the electroanatomic data 14 can be stored in a data structure of rows (corresponding to different anatomical points) and columns (corresponding to samples) in which the rows of data have the same index as (or are registered to) respective points residing on patient geometry data 16. This registration or indexed relationship between the electrical data 14 and the patient geometry data 16 is indicated by a dashed line at 18. In one embodiment the samples in each of the columns can represent simultaneous information across the entire surface region (e.g., the heart) of the patient.

The patient geometry data 16 can be generated from image data that is acquired using nearly any imaging modality. Examples of imaging modalities include ultrasound, computed tomography (CT), 3D Rotational angiography (3DRA), magnetic resonance imaging (MRI), x-ray, positron emission tomography (PET), and the like. Such imaging can be performed separately (e.g., before or after the measurements) utilized to generate the electroanatomic data 14. Alternatively, imaging may be performed concurrently with recording the electrical activity that is utilized to generate the patient electroanatomic data 14 or the imaging.

It will be understood and appreciated by those skilled in the art that the system 10 is equally applicable to employ anatomical data that may be acquired by any one of these or other imaging modalities. Alternatively or additionally, the patient geometry data 16 can correspond to a generic or custom representation of an organ, which may not be the patient's own organ. In such a case, the electroanatomic data 14 can be mapped (via registration 18) to the representation of the organ according to identified anatomical landmarks. A manual, semi-automatic or automatic registration process can be employed in order to register the anatomical model with the signal acquisition system, if any.

It further will be understood and appreciated that depending upon the format and type of input data appropriate formatting and conversion to a corresponding type of representation can be implemented by the system 10. For instance, the patient data 12 can include electroanatomical data that is provided to the system 10 in a known format or be converted to a standard format for processing by the system. Thus, the patient data 12 can include an aggregate set of electroanatomical data for the patient.

The system 10 includes an analysis system 20 that is programmed with methods 22, such as are programmed to identify, classify and visualize origins and mechanisms relating to patient electrical activity. The analysis system 20 provides output results data to an output device 24 that generates a corresponding visual representation 26 based on the output results data. The methods 22 can also be utilized to provide reliable and consistent targets for ablation and during all complex arrhythmias. Methods 22 can also be utilized to monitor change and organization of atrial activity such as during preoperative, intra-operative monitoring, and post-operative follow up. The system can employ methods that compute information for previously acquired data as well as data that is being acquired for real-time (or near real-time) analysis. For instance, the methods are useful for monitoring cardiac activity during ablation, analyzing ablation outcomes, and for post ablation follow up.

The system 10 also can include an interface 28 that can be employed to select which methods and algorithms are used as well as to control parameters associated with performing the methods and the resulting representation 26 that is displayed on the output device 24. For instance, the user interface 28 can enable a user to select one or more algorithms that are used to perform computations for use in populating an output representation generated in accordance with an aspect of the invention. A plurality of predefined and user-programmable algorithms can be employed to generate corresponding physiological data that can be visually represented to the user. Additionally, each of the algorithms can be programmed to compute corresponding physiological data for an assigned virtual electrode that has been positioned relative to a representation of the patient's organ (based on position data) such as described herein. A virtual electrode corresponds to a point on the patient's anatomy (epicardially or endocardially) of interest for which a selected method or combination of methods will be applied to patient electrical data for generating a corresponding output representation. Furthermore, the user can dynamically assign one or more algorithms, including digital signal processing algorithms per lead on the virtual electrode, or a general computation including statistical analysis on the aggregate of all or some of the virtual electrode's leads.

Each of the methods 22 can employ a corresponding user interface element, such as a graphical feature for activating a drop down menu or dialog. For instance, in response to activating the user interface element for a given algorithm, a user can access a corresponding programming dialog, which the user can employ to define properties and constraints associated with the selected algorithm. The properties can include setting one or more time intervals in response to which the resulting output data and corresponding visual representation are generated. The user interface 28 can also provide a user-entry dialog through which the user can enter associated constraints associated with the selected algorithm. The constraints entry dialog for a given algorithm can include a mechanism to select a subset of the electrodes as well as to define input or output limits associated with the algorithm.

Each of the methods 22 can define a type of information to be provided in the resulting output representation 26. The methods 22 can range in complexity from providing types of data that can be measured by an actual electrode (e.g., electrical potential) to providing more complex statistical and comparative types of information. One type of data can be considered a look-up or measured value, such as including electrical potential activation time or frequency of the electrophysiological signals for the selected electrode configuration. Other types of data can provide information that can be computed based upon such measured variables, such as including a gradient of any variable or the statistics of variables, such as including a mean, maximum or minimum. It is to be appreciated that any such variables or statistics thereof can be computed spatially with respect to the organ and the electrode configuration that is positioned relative to the organ as well as temporally over a time period in which the electrophysiology data has been acquired. The temporal range (or interval) can be defined as part of the constraints or properties for performing a given selected method or algorithm.

Additionally, there can be multiple output representations and an arrangement of these displays and the type of information that is being displayed can be controlled by the user. For instance, the user interface 28 can be utilized to access graphics control methods that are programmed to control, for example, whether the output is in a text based form or a graphical form that is superimposed over the select organ and relative to a graphical representation of the selected electrode configuration and/or waveform representation.

In addition to affording the user an opportunity to select any number of one or more algorithms and apply such algorithms to any number of one or more virtual electrode configurations, the methods 22 can include a compare function that can access methods and functions programmed to generate comparative data. The comparative data can be a spatial comparison (e.g., between different virtual electrodes or different anatomic positions), a temporal comparison (e.g., the same virtual electrodes at different instances in time), or a spatial-temporal comparison (e.g., different virtual electrodes at different time instances), which can vary depending on the type of data that is being compared. The compared data further can compare similar types of information derived for different virtual electrode configurations.

As an example of temporal comparative data, one or more measured values or derived values for a same given anatomic location (e.g., corresponding to the same virtual electrode configuration) can be compared for different cardiac intervals. For instance, a user can employ methods to provide a comparison of earliest activation time for a first interval relative to the earliest activation time for a second interval, which results can be displayed on an output representation either superimposed on the same representation of the patient's organ or as a side-by-side comparison on two separate representations of the patient's organ.

As yet a further example, where the original data set has been acquired as unipolar data, the methods can be used to generate corresponding bipolar data such as by subtracting electrophysiology data that had been determined between two different virtual electrodes. The two different virtual electrodes can be chosen automatically, such as each pair being chosen by applying a nearest neighbor algorithm. Alternatively, the virtual electrode pairs can be user definable, such as by using a pointer and selecting the electrodes or by identifying the electrodes by name in a text based data entry method.

In addition to applying a set of predefined algorithms such as described herein, the user interface 28 can also provide means for a user to construct a new user-defined algorithm. For example, a new algorithm can be constructed to define one or more characteristics, which can include measured types of variables and derived types of variables as well as to provide comparative relationships between selected electrodes. The new algorithm can be provided according to a defined scripting language that is utilized by the system.

One or more algorithms can also be utilized to dynamically determine or identify one or more anatomical locations that meet user-defined criteria, such as according to a user-selected algorithm or function range. The user can employ a method programmed to automatically generate the visual representation to include set of virtual electrodes (or other identifiers, such as a map) at anatomic positions of the patient's organ that satisfy user-defined criteria.

As a further example, the user interface 28 can provide means for a user to select a location on a graphical representation provided from the patient geometry data 16. The selected location can be translated to location data, such as can correspond to a three-dimensional position in a coordinate system that is consistent with the patient geometry data. As an example, a user can employ a cursor via a pointing device (e.g., a mouse) to identify and select a location on the two-dimensional graphical representation of the patient geometry. The 2-D screen location can be translated to a corresponding 3-D position on the model according to the selected location.

As mentioned above, the analysis system 20 is programmed to generate a visual representation output data by applying one or more of the analysis methods 22 to the electroanatomic data 14 and patient geometry data 16. For example, the output device 24 can be a display that provides the visualization 26 in the form of graphs, text or numerical values, which can be provided in separate windows adjacent to the graphical representation of the patient geometry data 16. Additionally or alternatively, the analysis system 20 can provides the output data to an output device that is configured to provide a corresponding visual representation (e.g., in the form of a graph or numerical value) that is rendered as an object graphically superimposed relative to the graphical representation of the patient model, indicated by arrow 30.

Figure 2:
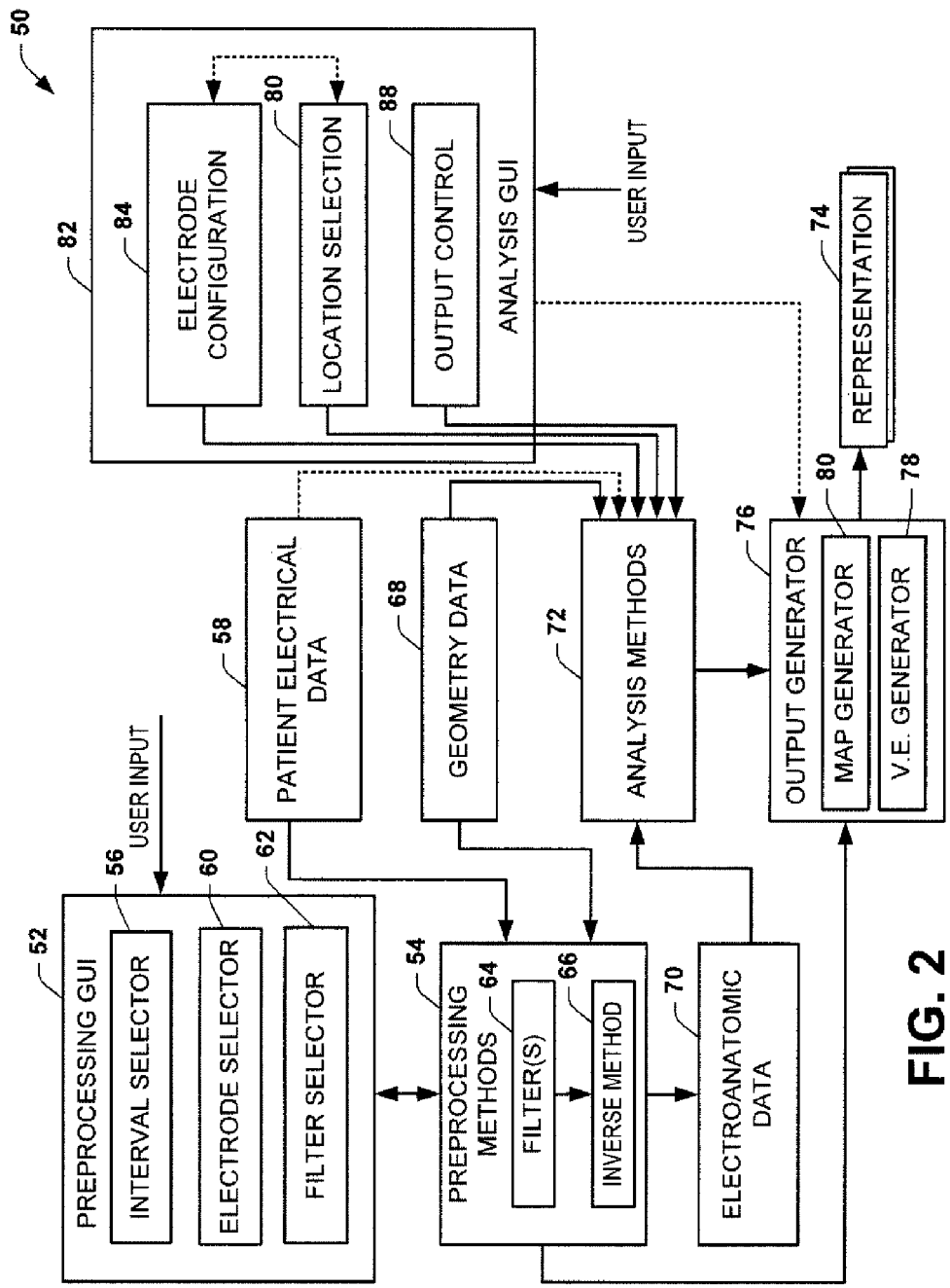
FIG. 2 depicts a block diagram of a system for visualizing physiological data for one or more virtual electrodes in accordance with another aspect of the invention.

FIG. 2 depicts an example of another system 50 for visualizing physiological data for a patient. In the example of FIG. 2, features of the system 50 for performing preprocessing as well as analysis and generation of visual representations are depicted. The preprocessing portions of the system 50 can be utilized to preprocess and convert the data to an appropriate form for an appropriate time interval such as can include one or more beats. The system 50 includes a preprocessing graphical user interface (GUI) 52 that is responsive to user inputs. The preprocessing GUI 52 can include a plurality of selection mechanisms each of which can activate corresponding preprocessing methods 54.

In the example of FIG. 2, the preprocessing GUI 52 includes an interval selector 56 that can be utilized to select one or more time intervals that may be of interest to the user. For example of electrocardiographic analysis, the intervals can correspond to beats or cardiac cycles any user defined time interval (e.g., a portion of one or more cycles) over which electrical data 58 has been acquired. As another example, the intervals can be non-temporally contiguous intervals, such as can be aggregated to provide a spliced signal having an increased frequency resolution due to the lengthened interval of the spliced signal.

As described herein with respect to FIG. 1, the patient electrical data can be acquired by various techniques, including invasive as well as non-invasive approaches. Thus, the patient electrical data 58 can correspond to substantially raw data that has been acquired for the patient, such as representing signals acquired for each of a plurality of electrodes.

The preprocessing GUI 52 can also include an electrode selector 60 that is utilized to select which electrode or electrodes are to be utilized to populate an output result set for use in further processing and analysis. The electrode selection can be automated, manual or a combination of manual and automated. The electrode selector 60 can be provided via a GUI that allows a user to selectively enable or disable each of the plurality of electrodes that have been utilized to acquire patient electrical data at a corresponding anatomic location. As an example, a plurality of electrodes can be distributed over a patient's torso for acquiring electrical information during a sampling period. Thus, the electrode selector can be employed to set which sensor or sensors will be utilized to acquire and define the subset of the patient electrical data 58. Automated methods can also be utilized to detect and remove bad channels.

The preprocessing GUI 52 can also include a filter selector 62 that can be utilized to select one or more preprocessing filters 64 for the selected set of patient electrical data 58. The preprocessing filters, for example, can include software methods programmed to filter the electrical data 58, such as including a low pass filter, DC removal filter, a de-trending filter, or a Wilson Central Terminal (WCT) filter. Those skilled in the art will understand and appreciate other types of filters 64 that can be selectively activated or deactivated via the filter selector 62.

As the filters are turned on or off or otherwise adjusted (parametrically), the filter methods 64 can be applied to the electrical data 58 and generate a corresponding filtered set of the patient electrical data (as also may be reduced according to the selected interval(s) and the electrodes that has been selected). After the filtering, electrode/channel selection and time interval selection have been implemented, the preprocessing GUI 52 (or other means or activation) can be utilized to activate an inverse method 66, such as described herein. The inverse method 66 utilizes geometry data 68 along with the modified patient electrode data (for the selected time interval, selected channels and filtered) to generate corresponding electrical anatomic surface data 70. The electroanatomic data 70 is indexed or registered relative to predefined surface region of a patient, such as an epicardial surface or an endocardial surface of a patient's heart.

Examples of inverse methods suitable for use with body surface electrodes are disclosed in U.S. Pat. No. 6,772,004, entitled System and Method for Non-invasive Electrocardiographic Imaging and U.S. patent application Ser. No. 11/996,441 (Now U.S. Pat. No. 7,983,743), entitled System and Method for Non-invasive Electrocardiographic Imaging, both of which are incorporated herein by reference. It will be appreciated that other approaches can be utilized to generate the electroanatomic data, which further may vary according to the mechanism utilized to acquire the patient electrical data 58.

The visualization system 50 also includes analysis methods 72 that are programmed to provide results data for generating a representation 74 of physiological data relating to the patient's organ. The representation 74 can be generated based the electroanatomic data 70 for the patient. The representation 74 may include graphics, text information, or a combination of graphics and text. It will be appreciated that the representation 74 provided by the system 50 is not limited to quantities actually measured or otherwise provided in the electroanatomic data 70, but can also correspond to electrophysiology data for a one or more virtual electrodes as may be selectively positioned by a user.

The analysis methods 72 can provide results data to an output generator 76 based on parameters established by a user, or preconfigured either by physician preferences possibly per procedure type. The output generator 76 is programmed to provide the representation(s) 74 in one or more forms, which can vary depending on the type of data being displayed.

As one example, the output generator 76 includes a virtual electrode (VE) generator 78 for providing the visual representation 74 responsive to a user selecting one or more locations in a predetermined surface region of a patient. Each selected location can correspond to a location in a coordinate system that can be defined or represented by the geometry data 68. For instance by selecting a location in a patient geometry coordinate system, corresponding electrical information in the electroanatomic data 70 for the nearest geometrical point (or a collection of nearest points) can be utilized by the analysis methods 72 to provide the results. The virtual electrode generator 78 in turn generates the corresponding representation of physiological data from the results of the analysis.

The representations 74 provided by the virtual electrode generator 78 can be considered spatially localized in response to a user selection, such as for providing data at a selected point (in the case of each single point virtual electrode) as well as along a plurality of user-selected locations corresponding to a multi-point or multi-dimensional virtual electrode. The representation of physiological data 74 generated for each virtual electrode can be in the form of graph, text/numerical information or a combination of graphs and text/numerical information. Any number of one or more representations can be generated for each virtual electrode.

The output generator 76 also includes a map generator 80 that is programmed for generating physiological data in the form of an electroanatomic map that is superimposed over the predetermined surface region of the patient's organ. For example, the map generator 80 can render one or more maps over the entire surface representation of the patient's organ, such as can be a two-dimensional or three-dimensional representation thereof. For instance, the map generator 80 can be programmable in response to a user-selection (e.g., via drop down context menu) to select which type of electroanatomic map will be generated.

The output generator 76 can provide the representation 74 as including information similar to that which might be generated based on electroanatomic data 70 provided according to any of the mechanisms described herein, including temporal and spatial characteristics that can be determined from acquired patient electrical data. As described herein, however, the system 50 enables the user to define a configuration of one or more virtual electrodes of a defined type and a location of such catheter(s) relative to the organ for which the representation 74 will be generated.

Additionally or alternatively, the configuration and placement of the virtual electrodes can be automatically selected by the analysis methods 72, such as to place an arrangement of one or more virtual electrodes at desired anatomic locations (e.g., landmarks), which can be defined by user-defined parameters. The user can also set parameters and properties to define what type of output or outputs the representation 74 will include. Thus, once the electrophysiology data has been acquired for a patient (using any technique) and stored in memory as the electroanatomic data 70, a user can employ the system 50 to virtualize physiological data of interest for the patient's organ. These results can be accomplished without requiring the user of the system 50 to actually acquire any new electrophysiology data from the patient. Thus, the system 50 can be a powerful addition to existing electrophysiology systems as well as can be utilized as a standalone system.

The system 50 includes an analysis user interface GUI 82 that is programmed to provide a human-machine interface for controlling and activating the analysis methods 72. A user can employ the GUI 82 via a user input device (e.g., a mouse, keyboard, touch screen or the like) to enter user inputs to set parameters and variables as well as to control display techniques and algorithms utilized by the analysis methods 72.

The user interface 82 can include a configuration component 84 that is utilized to define a configuration and arrangement of one or more electrodes for which one or more of the resulting representations 74 will be constructed. For example, the configuration component 84 can provide the user with an electrode configuration data set that includes a plurality of predefined electrode types. The predefined electrode configurations can correspond to any number of one or more electrophysiology catheters, which may correspond to commercially available products. For example, the predefined electrode configurations can correspond to any number of one or more electrode configurations that have been previously defined or constructed by a user or otherwise stored in memory as a library of available virtual electrode configurations. As described herein, the available electrode configurations can range from a single electrode (corresponding to a single point) or a linear arrangement of electrodes (such as disposed along a catheter or probe), two-dimensional (e.g., a patch or surface configuration) or three-dimensional electrode configurations (e.g., representing a volumetric arrangement of electrodes). These and other virtual electrode structures can be defined via the electrode configuration component 84. A user can also specify the number of electrodes and spatial distribution of such electrodes for a given configuration. As an example, a single electrode may be defined as a default setting for a virtual electrode, which can be modified to a different configuration via the configuration GUI 84.

The user interface 82 also includes a location selection component 86. The location selection component 86 can be utilized to identify one or more locations at which the selected electrode configuration (e.g., comprising one or more electrodes) is to be positioned relative to the patient's organ. For example, the location selection component 86 can employ a GUI element, such as a cursor, that a user can position with a pointing device (e.g., a mouse, touch screen and the like) to select a corresponding anatomical location on a graphical depiction of the patient's geometry. For example, the location can be on a selected surface region of an organ, in the organ or proximal to the organ. As described above, the representation 74 can be generated for the selected location based on the location data, electroanatomic data 70 for a given virtual electrode configuration.

As an example, in response to the user input, the location selection component 86 can cause a graphical representation of the selected electrode configuration (e.g., a single virtual electrode or an arrangement virtual electrodes, such as in the form of a catheter, a patch or other type electrophysiology measuring device) to be positioned at the selected location. The location selection component 86 can also be utilized to adjust the orientation (e.g., rotate) and position of the selected electrode structure relative to a two-dimensional or three-dimensional coordinate system for an anatomical model of the patient's organ. That is, as described herein, the selected location of a cursor on an image can be translated to a position (e.g., in a three dimensional coordinate system) relative to known patient geometry. Additionally or alternatively, the location selection component 86 can provide a list of one or more predefined common anatomical locations. The common locations can be programmable and include user-defined locations as well as those known in the art to be useful locations for visualizing electrical activity for the organ.

As a further example, in situations where a user is to define the virtual electrode configuration as a catheter having a single electrode or having a plurality of electrodes, the location selection component 86 can be utilized to identify a location at which the catheter is to be positioned. In response to the user identifying the location, the identified location can be populated with a graphical representation of the virtual electrode structure superimposed over the graphical representation of the interactive surface region of patient anatomy. Additionally or alternatively, the cursor itself can also take on the form of the selected virtual electrode construct, such as while it moves across a window in which the organ model is being displayed.

In addition to selecting a desired location at which a virtual electrode is to be positioned, the location selection GUI 86 can provide means for a user to draw a contour or a closed surface at a desired location on the graphical representation of the patient's organ (e.g., on the left ventricle of the heart). The resulting contour or closed surface can identify a corresponding path or boundary for a virtual electrode structure. For a contour, the length of the contour can be automatically populated with an arrangement of virtual electrodes. Similarly, an interior of the patch boundary can be automatically populated with an arrangement of electrodes. The spatial distribution and number of electrodes can be specified by the user (via the electrode configuration component 84). The arrangement and spatial distribution of electrodes for a given configuration can be uniform (e.g., as a default setting) or it may be non-uniform, as programmed by a user.

The user interface 82 can also include an output control component 88 that is utilized to set output parameters and properties for each representation 74 that is generated. The output control component 88 can be utilized to select one or more measured or derived electrophysiology parameters that can be provided as part of the representation 74 based on the electrode configuration data and location data for each virtual electrode configuration. The output control 88 can be programmed to provide the employ the same algorithm for each virtual electrode or, alternatively, different algorithms or constraints can be defined for each virtual electrode. The results set for the selected output control can include electrical potentials (e.g., unipolar or bipolar electrograms, activation times, frequency information (e.g., power spectrum), and statistics relating to these as well other derived quantities.

Another application of the output control component 88 can be to selectively swap electrode configurations for comparative purposes. For example, the output control component 88, individually or in combination with the electrode configuration component 84, can be employed to add or remove as well as to reposition two or more selected catheters relative to the representation of the patient's organ to modify the results provided in the output representation 74.

The output control 88 further may be utilized to implement comparative functions between algorithms, between temporal sets of different electrophysiology data or to otherwise constrain the resulting output data that is to be visualized on the output device.

By way of example, the output representation 74 may include the statistics of activation within a region of the patient's organ (e.g., as defined by placement of a 2-D virtual electrode or a virtual patch), including a minimum, a maximum, an average, and a standard deviation of activation time, a minimum, maximum, average and a standard deviation of the electrical potential. Those skilled in the art will appreciate that other statistical analyses or properties may be part of or derived from the electroanatomic data 70.

As a further example, the output control 88 can be utilized to control or establish a filter that controls what information will be utilized by the analysis methods 72 to generate a corresponding output representation 74. For instance, a user can employ the output control 88 to set an interval for ascertaining activation time or other constraints for each virtual electrode. As another example, an interval can be set by a user that is utilized to determine a dominant frequency for each virtual electrode. A corresponding dominant frequency map can also be generated. Thus based on such constraints, locations (corresponding to anatomical positions) that satisfy such time limits or other constraints can be determined and provided to the output device for display graphically (or otherwise) on a graphical representation of the organ. It will be thus appreciated that any type of data that can be measured or computed for an electrode arrangement positioned relative to a patient's organ can be computed and be provided in a virtual environment based on electroanatomic data 70.

Preprocessing of Electrophysiology Signal Data

As explained herein with respect to FIGS. 1 and 2 various types of preprocessing can be performed on input electrical data, such as including interval selection and filtering.

Figure 3:
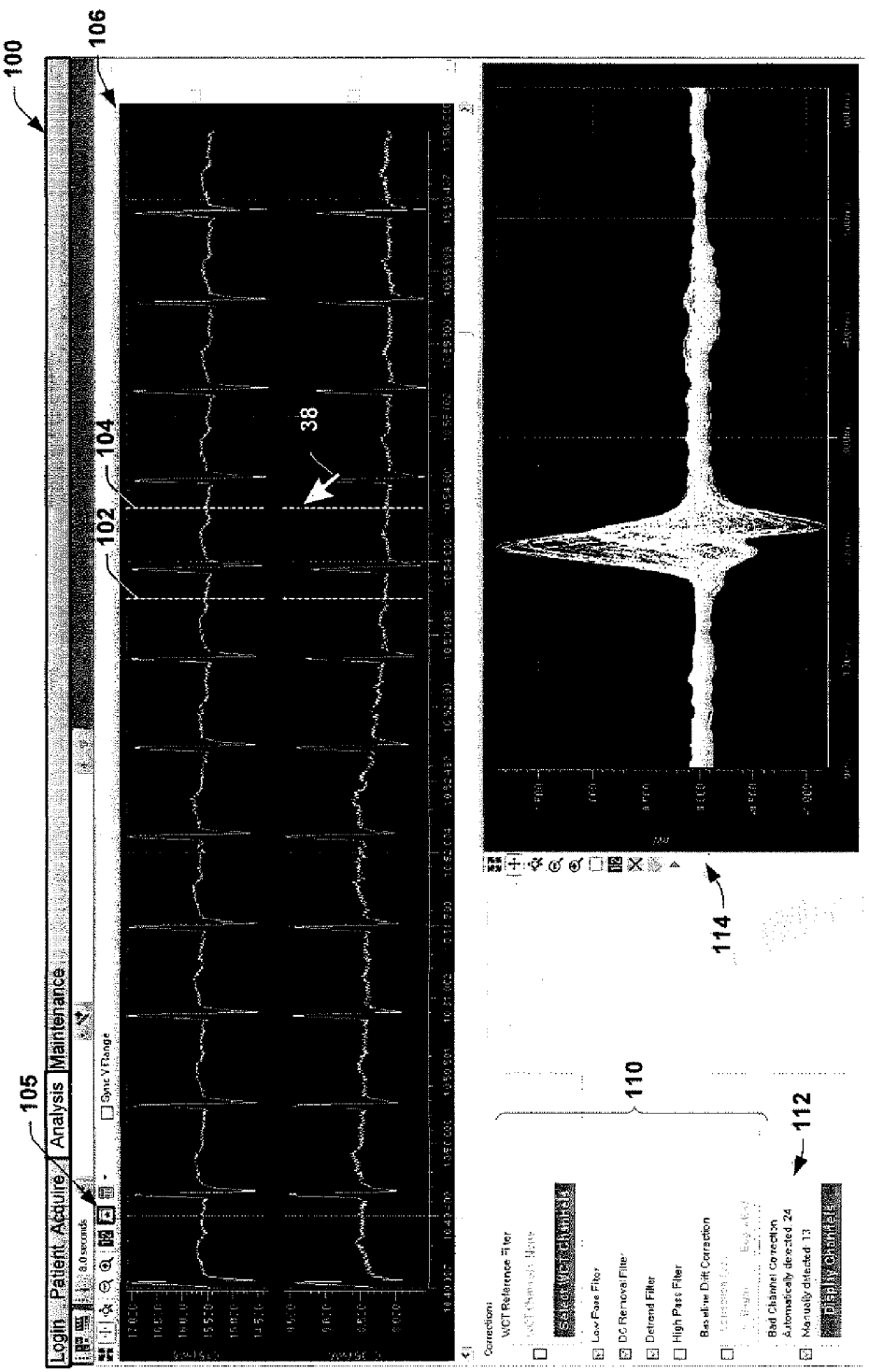
FIG. 3 depicts an example of a GUI that demonstrates some types of preprocessing that can be implemented in a visualization system according to an aspect of the invention.

FIG. 3 depicts an example of a portion of a pre-processing GUI 100 that can be implemented for the system 50 of FIG. 2. The preprocessing GUI 100 includes interval selection and filter selection GUI elements. In the example of FIG. 3, an interval selection is determined by placement of calipers 102 and 104 in the waveform window 106. While two waveforms are illustrated in the window 106 in this example, those skilled in the art will appreciate and understand that any number of such waveforms can be depicted in the GUI 100 and that the number of waveforms can be selected by the user. The interval calipers 102 and 104 can be initially positioned at a given location in the waveform window 106, such as in response to activating an interval selection user interface element 105. A user can adjust the caliper positions via a cursor (or other pointing element) 108. Thus, by adjusting position of one or both of the respective calipers 102 and 104 a desired interval or beat can be selected by the user for further processing as described herein. While a single interval is illustrated in FIG. 3 by calipers 102 and 104, it is to be understood and appreciated that any number of one or more such intervals can be selected for additional types of processing (See, e.g., FIGS. 4 and 5). The set of patient electrical signals for the selected interval are shown in a window 114 for each of the active channels. Thus, in the window 114, the signals for each of the channels for the selected time period (defined by the interval) are shown according to filtering and other correction factors that are applied to the set of signals.

Also depicted in FIG. 3 are filter selection GUI elements 110, such as corresponding to the filter selector 62 of FIG. 2. In the example of FIG. 3, various types of corrections and filtering can be selectively performed dynamically on patient electrical data, including are the WCT reference filter, low pass filtering, DC removal filter, de-trending filter, a high pass filter and baseline drift correction. Thus selecting a given filter activates corresponding filtering methods on the patient electrical data.

Additionally, bad channel correction may be implemented via GUI elements 112, such as if data appears outside of expected operating parameters. The bad channel correction GUI elements 112 can be activated to implement an automatic method that detects and selects waveforms determined to correspond to bad channels (or bad electrodes). Additionally, waveforms can be selected manually for removal from the corresponding graphical waveform window 114 if they appear anomalous relative to the other waveforms. Those skilled in the art will appreciate various approaches that can be implemented to remove the anomalies or bad channels can be removed from the sensor data.

Figure 4:
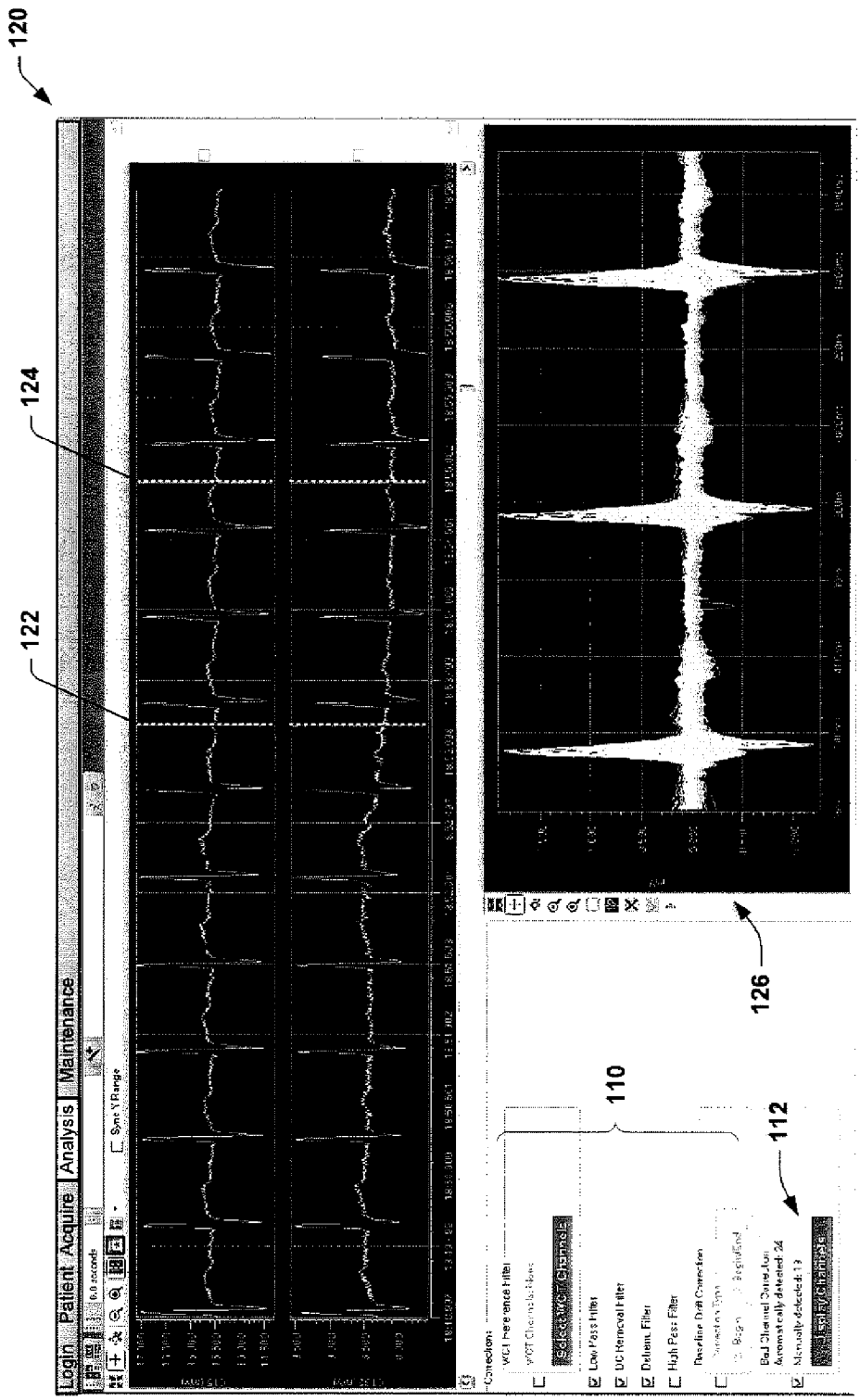
FIG. 4 depicts an example of a GUI that demonstrates additional types of preprocessing that can be implemented in a visualization system according to an aspect of the invention.

FIG. 4 depicts an example of a portion of a pre-processing GUI 120 that can be utilized to select an interval that includes more than one contiguous cycle. The basic form of the GUI 120 is similar to that shown and described with respect to FIG. 3. Accordingly, identical reference numbers refer to corresponding features previously introduced herein.

In the example of FIG. 4, a corresponding interval is defined by the relative position of calipers 122 and 124. A corresponding sample time period of signal segments is shown in the adjacent display window 126. As described herein, the set of signal segments in the window represent patient electrical data within a corresponding time period selected via the calipers 122 and 124. In this example, a single interval encompasses a plurality of beats or cycles for each of plurality of channels. The number of channels represented as signal segments in the window 126 can be controlled by the user as well as other types of preprocessing, as described herein. By selecting a greater time period (e.g., more than one cycle or beat) for subsequent analysis additional types of temporal analysis and corresponding spatial visualization of information can be realized.

Signal Splicing

During analysis of unipolar atrial signals especially in the case of atrial fibrillation, systems and methods can use segments of atrial signals between ventricular complexes. During frequency analysis of atrial signals, if the ventricular rate is too high then the length of atrial segment is too short thereby affecting the frequency resolution. Length of the signal is directly related to the frequency resolution, for a given sampling frequency. For example, for a sampling frequency of 1000 Hz and signal length of 1000 samples, the frequency resolution is 1 Hz. Smaller segments of non-temporally contiguous segments data can be spliced or aggregated to obtain an improved frequency resolution. Frequency components introduced due to splicing time domain signals that are not in reality continuous in time are negligible due to the relative randomness in comparison to the dominant periodicity of the atrial signals.

Figure 5:
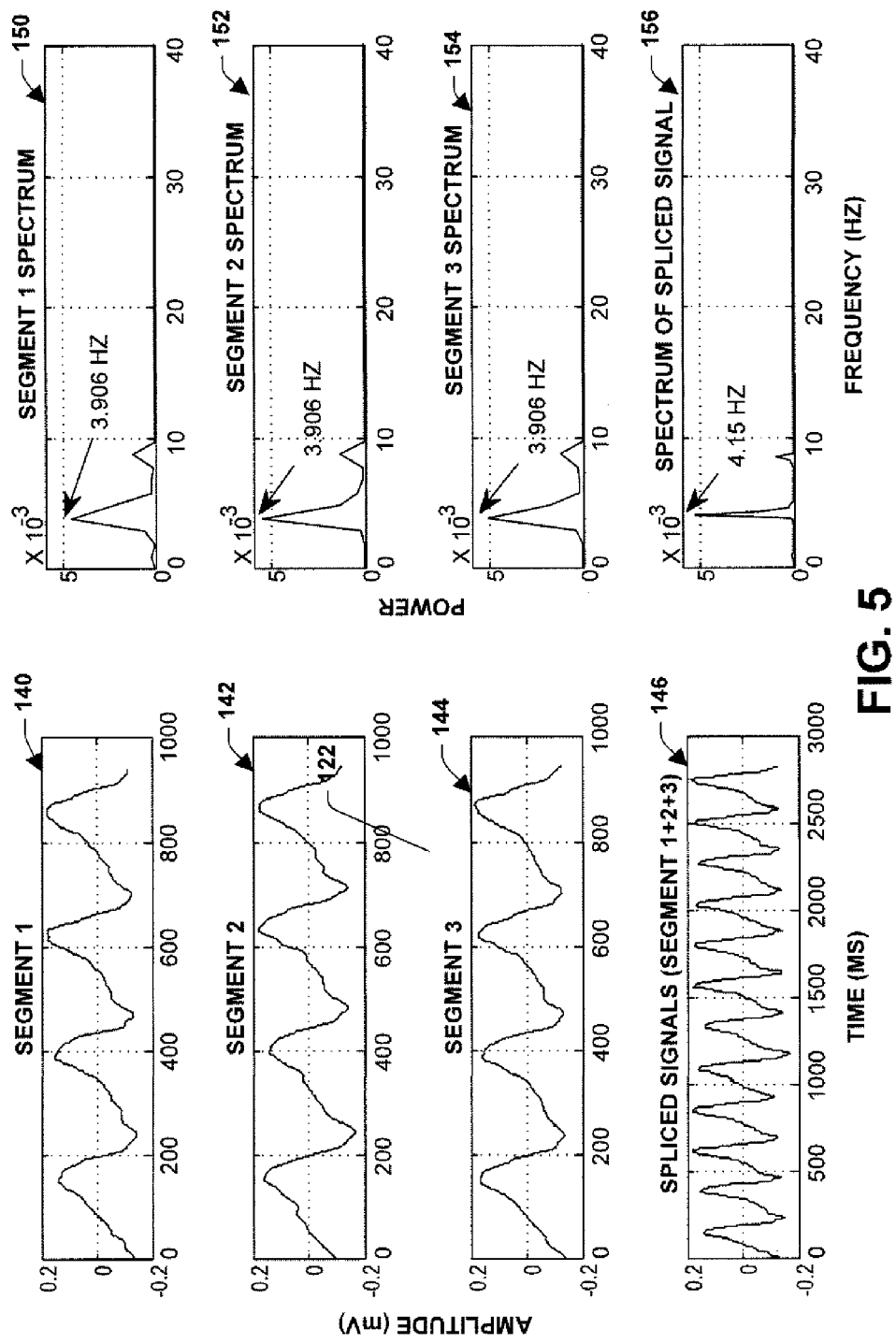
FIG. 5 depicts graphs demonstrating methods relating to signal splicing that can be implemented according to an aspect of the invention.

FIG. 5 depicts examples of signal segments 140, 142 and 144 and a resulting spliced signal 146 that can be determined according to the methods mentioned above. The signal segments 140, 142 and 144 demonstrate amplitude as a function of time, which time can be selected as described herein via an interval selector. Also depicted in FIG. 5 are examples of power spectra 150, 152, 154 and 156 (e.g., power or amplitude versus frequency) for each of the signal segments 140, 142 and 144 and the spliced signal 146, respectively. Also shown in the power spectra 150, 152, 154 and 156 is a corresponding dominant frequency for each of the respective signal segments 140, 142, 144 and the spliced signal 146. Thus, it is demonstrated that the spliced signal segment 146 contains increased resolution of frequency information due to the lengthier sample in the spliced signal.

Figure 6:
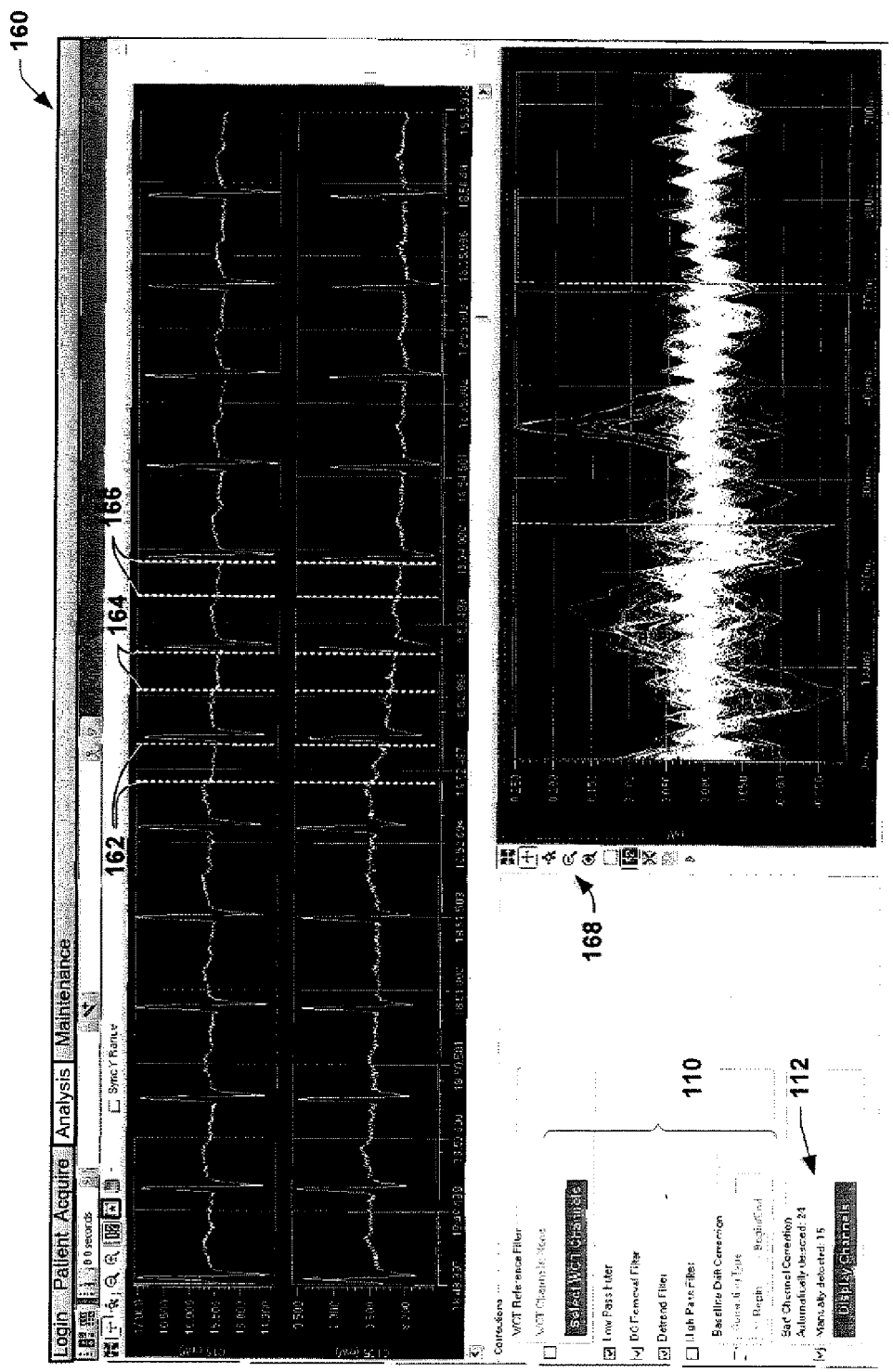
FIG. 6 depicts an example of a GUI that demonstrates preprocessing that can be implemented for selecting multiple intervals for splicing signals in a visualization system according to an aspect of the invention.
Figure 7:
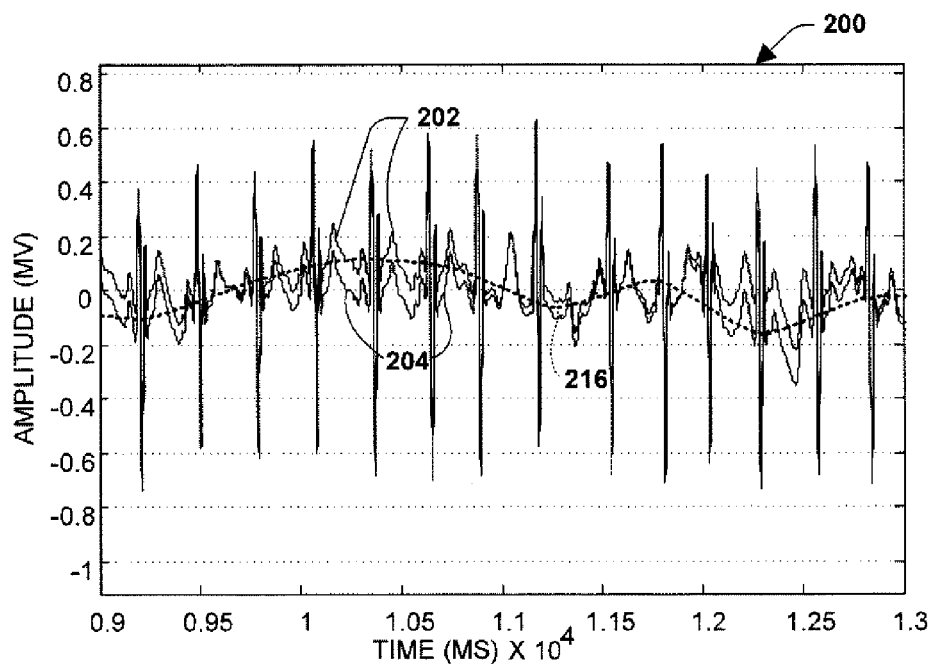
FIG. 7 is a graph depicting amplitude as a function of time for acquired signals demonstrating filtering and baseline drift correction that can be implemented according to an aspect of the invention.

FIG. 6 depicts an example of a preprocessing GUI 160 that is utilized to select multiple non-temporally contiguous intervals of electrophysiology waveforms that can be spliced together. The basic form of the GUI 160 is similar to that shown and described with respect to FIG. 3. Accordingly, identical reference numbers refer to corresponding features previously introduced herein.

In the example of FIG. 6, a plurality of non-temporally contiguous intervals are selected via the relative position of calipers 162, 164 and 166. A corresponding sample time period of signal segments is shown in the adjacent display window is shown in the adjacent display window 168. As described herein, the signals in the window represent patient electrical activity for spliced signal segments for each of the channels of patient electrical data. As a result, the signal segments provide an increased resolution for frequency analysis, such as described herein.

Baseline Removal

Another feature of preprocessing is baseline correction or baseline removal, such as can be activated on selected patient electrical data via filtering user interface elements (e.g., filter functions 110 in FIGS. 3, 4 and 6).

Signals are often contaminated with baseline drifts that cannot be removed with a simple high pass filter. The baseline correction method involves a technique of signal conditioning using multiresolution analysis (MRA) using wavelet transforms to remove extraneous baseline drifts while preserving the relevant signal content. During MRA of the ECG signal using wavelets, scaling and wavelet functions are obtained, which are associated with half band low-pass and high-pass filters, respectively. Baseline drift is substantially removed by eliminating the particular scaling coefficients of the wavelet transform that represent the level of the baseline drift.

Figure 8:
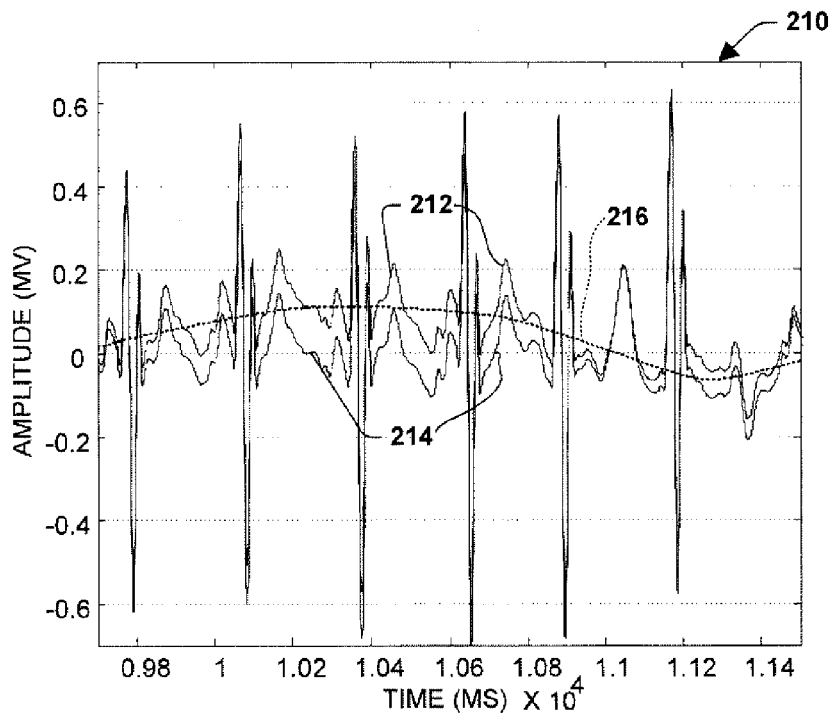
FIG. 8 is another graph depicting amplitude as a function of time for different acquired signals demonstrating filtering and baseline drift correction that can be implemented according to an aspect of the invention.
Figure 9:
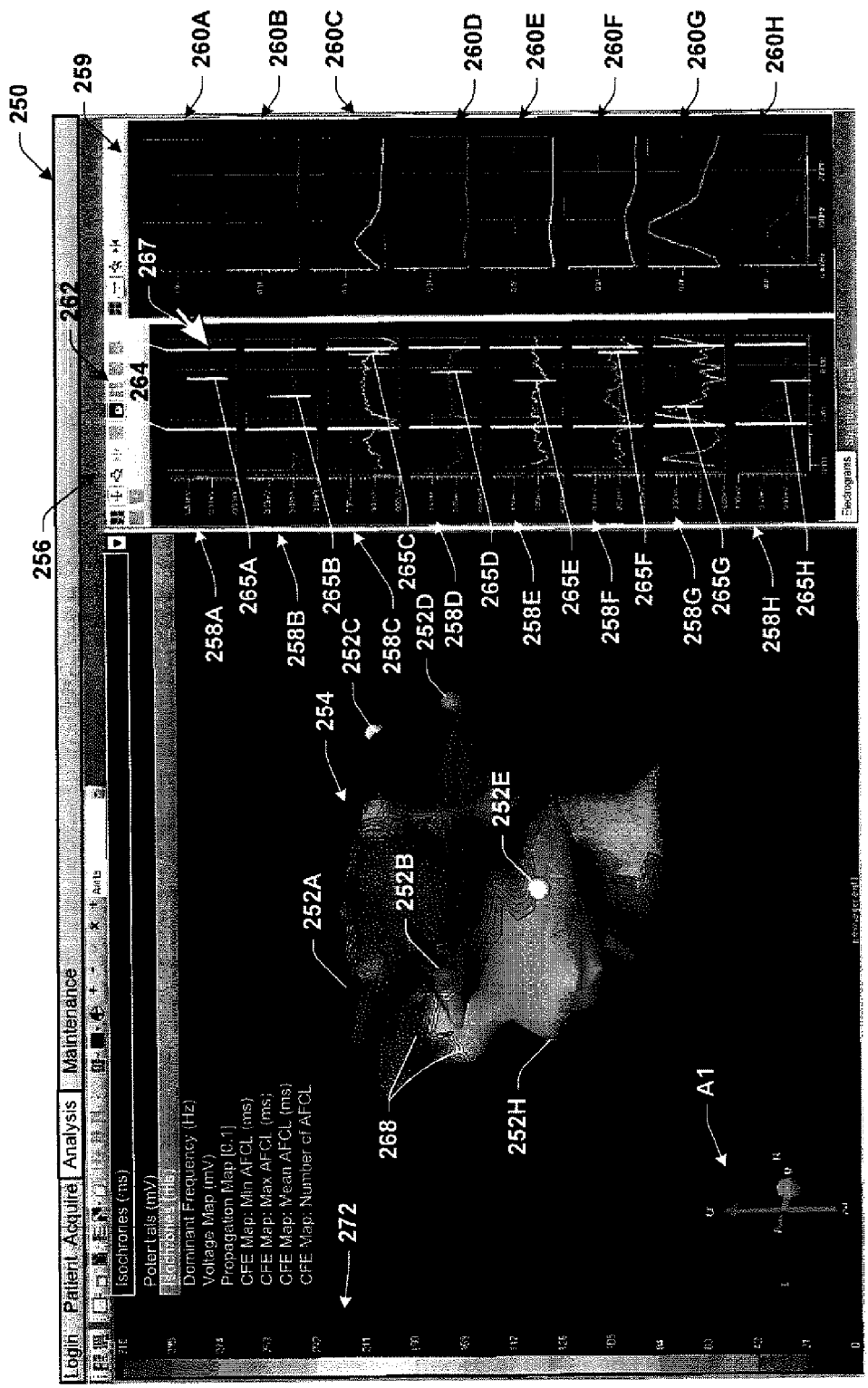
FIG. 9 depicts an example of a graphical user interface demonstrating visualization of activation time information according to an aspect of the invention.

FIGS. 8 and 9 depict representative plots of voltage amplitude as a function of time demonstrating application of preprocessing techniques. FIG. 8 depicts a plot 200 that includes an original signal 202, a filtered signal 204 and a signal 206 corresponding to computed baseline drift associated with the original signal. Similarly, FIG. 9 depicts a plot 210 that includes an original signal 212, a filtered signal 214 and a signal 216 corresponding to computed baseline drift associated with the original signal. By identifying the baseline drift 206 and 216 for each of a plurality of signals, corresponding scaling components of the wavelet transform can be eliminated to substantially remove the baseline drift from each such signal.

By way of further example, the length of the ECG signal determines the maximum number of levels of decomposition for MRA. And each level of decomposition has a particular band of frequencies associated with it. For a given sampling rate, for example 1000 samples/sec, the ninth level of decomposition will consist of frequency components from [0, 1] Hz and for the tenth level of decomposition it would consist of frequency ranging from [0, 0.5] Hz. The baseline drift (low frequency components) appear on the scaling coefficients. For example drifts in the signal representing frequencies below the 1 Hz band can removed by eliminating the scaling coefficients corresponding to ninth level of decomposition.

Analysis Methods and Associated Visualizations

The following are descriptions of some of the methods that can be utilized by an analysis system (e.g., FIG. 1 or 2) to provide corresponding spatial visualization of physiological data according to an aspect of the invention.

Activation Time

The analysis methods shown and described herein (e.g., FIGS. 1 and 2) can be programmed to compute an activation time for one or more selected location on the surface of the patient's organ in response to a user-selected interval. The activation time can also be computed for each point on the patient's organ for which electroanatomic data has be acquired or computed for a corresponding time period. A user thus can select an interval in response to a user input (e.g., via pointing user interface element). The interval can be modified in response to further user inputs that change the interval or the interval may remain fixed if no changes are made to the interval.

The activation times can be presented as site-specific data at any spatial location on the heart using a virtual electrode function associated with the GUI. The data can be presented as a 3D map or animation, showing wavefront propagation corresponding to spatially distributed activation times (e.g., a star map) such as shown and described with respect to FIG. 16. A variation of this propagation map is the activation cine map. Here the user selects a fixed cycle length interval on the electrogram. The electrogram is moved step by step through this interval to generate a dynamically changing visualization of the isochrones map for each step of the electrogram through the interval.

FIG. 9 depicts an example of a GUI 250 demonstrating a visualization of activation time presented as an isochrone map superimposed over a graphical representation of a surface of a patient's heart 254. In the example GUI 250 of FIG. 9, a plurality of virtual electrodes 252A, 252B, 252C, 252D, 252E, 252F, 252G and 252H have been positioned at user-selected locations on representation of the patient's heart 254. It will be appreciated that, as described herein, any number or configuration of virtual electrodes can be positioned on the surface 254. Adjacent to the window in which the surface representation 254 is depicted, are additional analysis and evaluation tools.

In the example of FIG. 9, an electrogram window 256 is populated with an electrogram 258A, 258B, 258C, 258D, 258E, 258F, 258G and 258H for each of the virtual electrodes 252A, 252B, 252C, 252D, 252E, 252F, 252G and 252H, respectively. Thus, each electrogram displays the electrical activity (voltage versus time) according to the electroanatomical data determined for each point at which the respective virtual electrodes are positioned.

Additionally depicted in FIG. 9 is a window 259 that includes power spectrums graphs 260A, 260B, 260C, 260D, 260E, 260F, 260G and 260H for each of the virtual electrodes 252A, 252B, 252C, 252D, 252E, 252F, 252G and 252H. Power spectrum demonstrates frequency versus amplitude, such as can be computed from the electrograms 258A, 258B, 258C, 258D, 258E, 258F, 258G and 258H associated with each of the respective virtual electrodes 252A, 252B, 252C, 252D, 252E, 252F, 252G and 252H.

Figure 10:
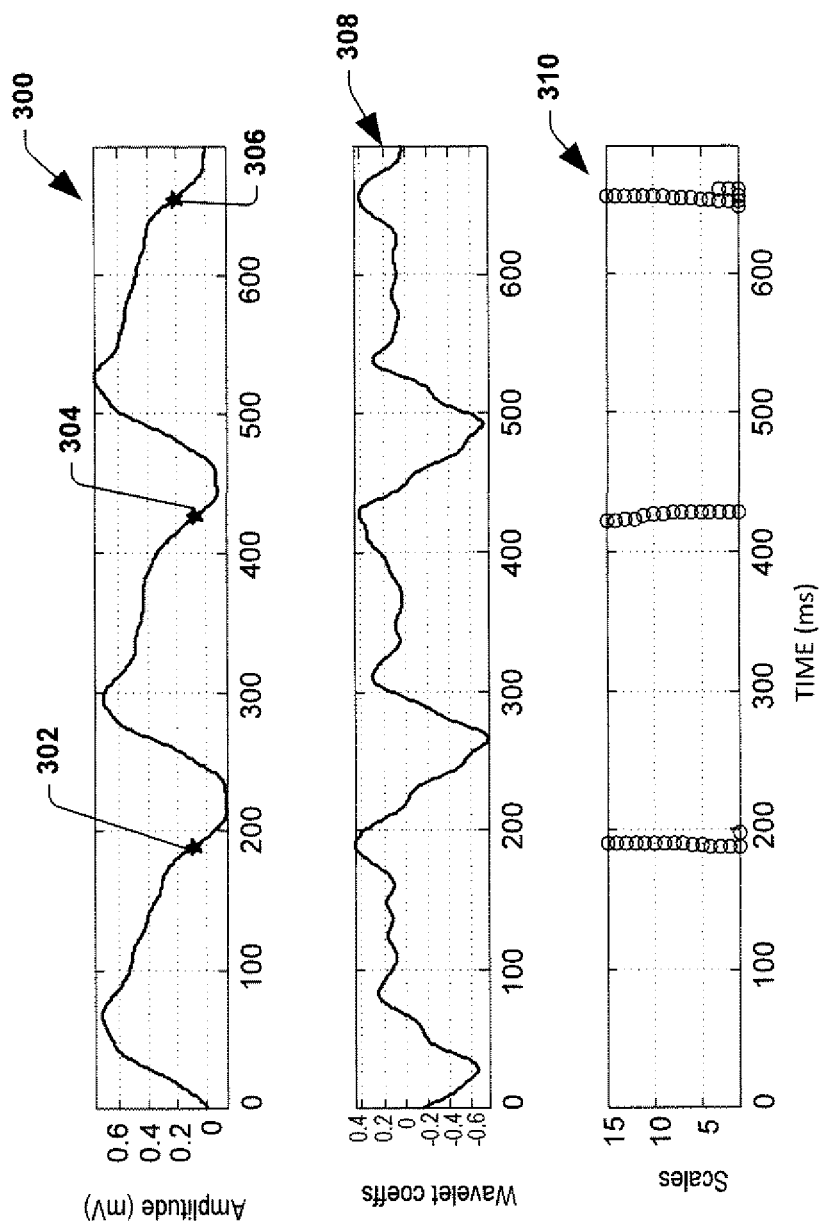
FIG. 10 is an example of an electrogram demonstrating plural activation times and corresponding cycle lengths that can be determined according to an aspect of the invention.

Additionally in the example of FIG. 10, a coordinate axis A1 is depicted adjacent to the surface model demonstrating the relative orientation of the patient's heart model 254. A user can further rotate the three-dimensional surface model 254 (e.g., via the cursor or other image controls) to a desired orientation for selecting and applying virtual electrodes to one or more selected surface region.

The GUI 250 also includes a mechanism to define a time interval relative in the electrogram window for which activation times can be computed. For example, in response to a user selecting an interval selection user interface element (e.g., a button) 262 a caliper user interface element 264, which defines start and stop times, can be provided onto each electrogram in the electrogram window 256. In response to such user selection activating the interval selection function, an activation time can be computed according to the selected interval. An indication of the activation time can be provided for each of the electrograms according to the specified interval. Activation time for each of a plurality of points on the entire surface of the heart can be computed for the interval and a corresponding activation (or isochrone) map can be generated to spatially represent the activation times over the surface 254, as shown. The isochrone map 268 depicts activation times that have been computed as a function of an interval selected (via GUI element or button 262) in the electrogram window 258. A graphical scale (or color key) 272 can be provided adjacent to the isochrone map 268 to inform the user of what each shade or color in the map represents. The computed activation time for each electrogram is also represented at 265A, 265B, 265C, 265D, 265E, 265F, 265G and 265H for each respective electrogram 258A, 258B, 258C, 258D, 258E, 258F, 258G and 258H.

As demonstrated in FIG. 10, the caliper user interface element 264 can include a first caliper that defines a first time for the interval and a second caliper that defines a second time for the interval, such that the difference between times defines the time interval. This time interval can be common for each of the electrograms, as demonstrated in the figure. A user further may modify the time interval resulting in corresponding changes to the activation time being displayed in the activation map that is superimposed on the patient's heart. For instance, a user can employ the cursor 267 to selectively adjust one or both of the calipers 264 to adjust the interval in the displayed electrograms. In response to the changes in a given caliper, the selected interval of the electrograms changes. As the calipers 264 are adjusted, a corresponding activation time can be re-computed for each of the electrograms 258A, 258B, 258C, 258D, 258E, 258F, 258G and 258H for the respective virtual electrodes. The activation time for each of the plurality of points (e.g., thousands of points) is similarly computed in response to the changes in the interval. A corresponding method for computing the frequency spectrum can also be reapplied in response to changes in the user-selected interval. The visual representation (e.g., the electroanatomic map superimposed on the heart) is dynamically modified responsive to changes in the user selected interval.

By way of further example, the activation time can be computed by analyzing the change in voltage over time (e.g., dV/dt) within the selected time interval. Alternatively or additionally, such as depending upon the type of waveform, wavelet analysis can be performed to ascertain the activation time for a given waveform. For instance, in atrial fibrillation, however, the cycle lengths are not identifiable from the chaotic fractionated waveform, resulting in the need for activation time methods which are independent of cycle length and can identify one or more activation times in a given electrogram within an interval or in real-time.

An analysis system according to an aspect of the invention can include methods programmed to employ wavelet analysis to identify all local activations present in the given electrogram. That is, wavelet analysis can determine any number of one or more local activations that may exist in a respective waveform. Such analysis utilizes specially designed wavelets (referred to as 'intrinsic wavelets'). The intrinsic wavelets are, representative of local activation. Then, one or more electrograms from all or select locations are decomposed via wavelet transformation with step-wise scaled and translated versions of the intrinsic wavelet. Resultant wavelet coefficients are analyzed for each time frame of the electrogram. At smaller scales, wavelet coefficients reflect the details in the signal including the intrinsic deflection. At lower to middle scales, wavelet coefficients reflect bundles of myocardium in the neighborhood of said electrogram(s). At larger scales, the wavelet transform is partial to the global structure of the electrogram. Local intrinsic deflections are omnipresent in the signal and therefore reflected through all decomposition levels. The multiple activation time detection methods exploit this property to identify local activity and assign the corresponding time frame(s) as a plausible activation time(s). If no time instant satisfies this wavelet criteria, no activation time is assigned to that site. This further can help automatically identify regions of no activity (e.g., like scar tissue).

As a further example, variation of wavelet coefficient curves with respect to time for each scale is computed. Peaks of the curve are detected and dominant peaks within a specified threshold of the maximum peak ('peak-threshold') are selected for each scale. Time frames within a specified tolerance or width ('window-width') at which peaks are registered across all scales are selected as activation times. Translation can be at the electrograms' original sampling frequency or be up-sampled or down-sampled. The peak-threshold can be adjusted to include fewer peaks or more peaks. Similarly, the window-width is user-programmable and thus can be made more stringent or more flexible.

Multiple methods can be programmed for detecting activation time. A given one of the programmed methods can be selected depending on whether the cycle length of a given electrogram can be readily ascertained. Those skilled in the art thus will appreciate that different methods for computing activation time can be selectively employed to each of the electrograms. For example, dV/dt computation can be utilized for determining activation time for each electrogram having an identifiable cycle length, whereas wavelet analysis can be utilized for electrogram for which the cycle length cannot be ascertained.

FIG. 10 depicts an example of plots showing an electrogram 300, a wavelet coefficient curve 308 and a plot of chained wavelet coefficients 310, such as can be computed based on the methods described herein. The computed activation times for the electrogram segment 300 are demonstrated by stars at 302, 304 and 306. Those skilled in the art will understand that a system or method can be programmed to selectively implement one or more methods of calculating activation, such as described herein.

Figure 11:
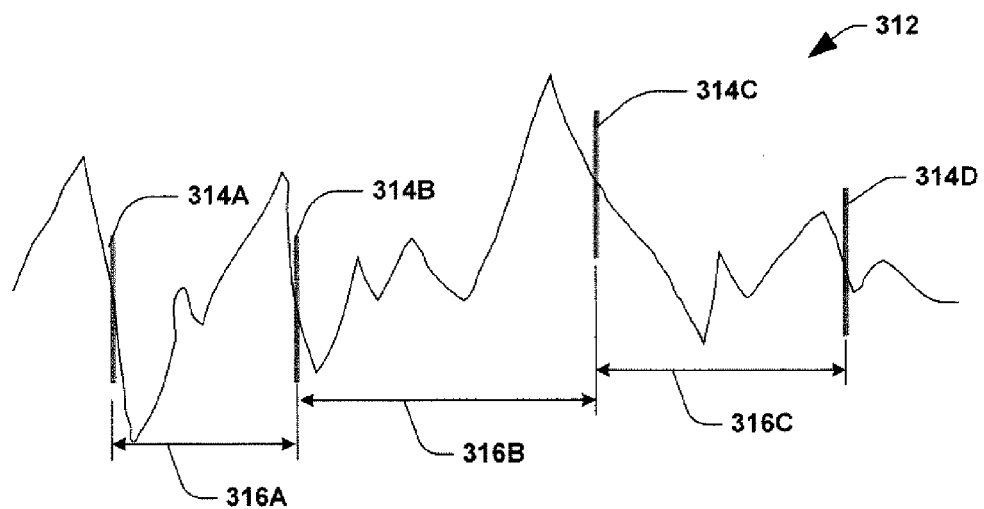
FIG. 11 depicts an example of graphs demonstrating an approach that can be utilized for determining activation times according to an aspect of the invention.

Additionally, activation times for a signal segment can be employed to compute cycle length as well as related statistical quantities for each of a plurality of points on a surface region of the patient's heart, including over the entire epicardial surface. By way of example, FIG. 11 depicts an example of a selected interval of an electrogram waveform 312. One or more activation times 314A, 314B, 314C and 314D can be computed for the electrogram 280 based on any one or more of the methods disclosed herein. Thus, in the example of FIG. 11, four activation times have been determined for the interval of the electrogram. A temporal distance between each sequential pair of electrograms corresponds to a cycle length between the pair of activation times, indicated at 316A, 316B and 316C. The number of activation times, the cycle length information and quantities computed based on such information can be spatially represented (e.g., on an electroanatomical map), such as shown and described herein.

It will be appreciated that such cycle length analysis is applicable for complex fractionated electrograms (CFE, see, e.g., FIG. 16) as well as other types of electrograms that may be characterized by simpler organized rhythms. Additionally, while the methods described herein have been described as being utilized for unipolar electrograms, those skilled in the art will understand and appreciate that the same methods can also be utilized for bipolar electrograms.

As also described herein, signal pre-processing to extract relevant frequency components may be applied in certain cases. These include baseline correction techniques, for example, including: DC offset removal via subtraction of the temporal mean, zero-correction of the beginning and end of callipered waveform(s), high pass filtering at <1 Hz cutoff, and adaptive filtering techniques like moving average and Kalman filtering, which could be considered as effective lower frequency band limiters. Low pass filters at >30 Hz cutoff and specialized filters like the Savitzky-Golay filter can be considered as effective higher frequency band limiters.

A variation of the wavelet analysis is to detect the absolute maximum transform coefficient across the entire electrogram and assign the corresponding time frame as the activation time. Another variation is to perform a further detailed wavelet analysis on time frames with dominant coefficients at lower scales.

Frequency Analysis

Methods described herein outline ways of extracting and analyzing the frequency spectrum of complex cardiac electrical activity. Frequency mapping facilitates the identification and localization of sites of fast and frequent activity that are associated with 'triggers' that sustain fibrillatory conduction. A first step in frequency analysis is to perform band-limiting the electrogram signal to a band of relevant frequencies. Lower frequencies to be removed include baseline variations due to DC offset, respiration and others.

Baseline correction techniques including DC offset removal via subtraction of the temporal mean, zero-correction of the beginning and end of callipered waveform(s), high pass filtering at <1 Hz cutoff, adaptive filtering techniques like moving average and Kalman filtering could be considered as effective lower frequency band limiters. Low pass filters at >30 Hz cutoff and specialized filters like the Savitzky-Golay filter can be considered as effective higher frequency band limiters. Band pass filters that limit the signal within bands of 0.5-30 Hz also can be considered instead of the above mentioned two step filtering process.

Next, Fast Fourier Transform (FFT) is used to extract the frequency spectrum of the electrogram(s). FFT can be computed using the highest power of 2 closest to the length of input signal (N) and the first (N+1)/2 points are extracted. Then the magnitude of the FFT is scaled by the length so that it is not a function of N and then squared. Since only the first half of the spectrum is needed to be used (as the second half is redundant), the energy of the entire spectrum is factored in by multiplying by two. If the DC component and Nyquist component exist (i.e., N is even), they are unique and are therefore not multiplied by 2. The FFT can be performed at the signal's original sampling frequency (e.g. at 1000 Hz) or be up-sampled or down-sampled. The length of the signal can be extended by zero-padding in certain cases to improve frequency resolution. Electrogram segments not continuous in time can be spliced and frequency analysis performed on the resultant combined signal (described in section 'splicing'). Frequency analysis of electrograms can be performed real time and continuously by using techniques for removal of intermittent ventricular activity ('QRS subtraction').

Figure 12:
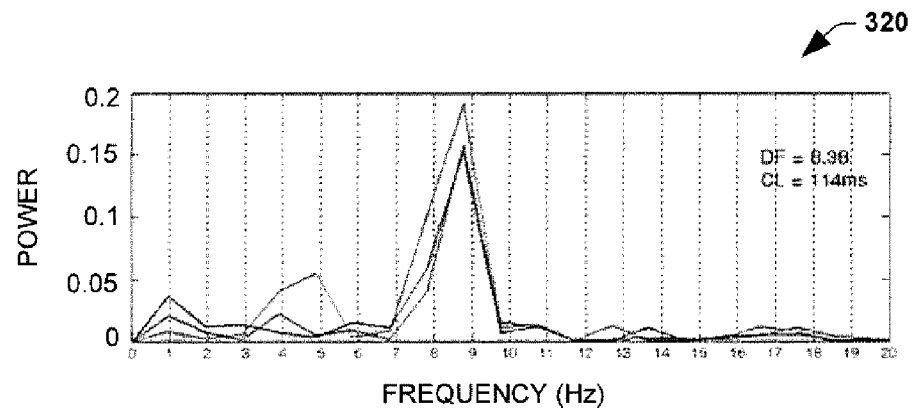
FIG. 12 depicts an example of a graph of a power spectrum.

The frequency spectrum computed at each spatial location on the heart can be recalled by reverse lookup and through the virtual electrode function of the GUI. From the frequency spectrum of each electrogram, the strongest power is designated as the Dominant Frequency (DF). An example frequency spectrum, demonstrating power versus frequency is shown in FIG. 12.

Figure 13:
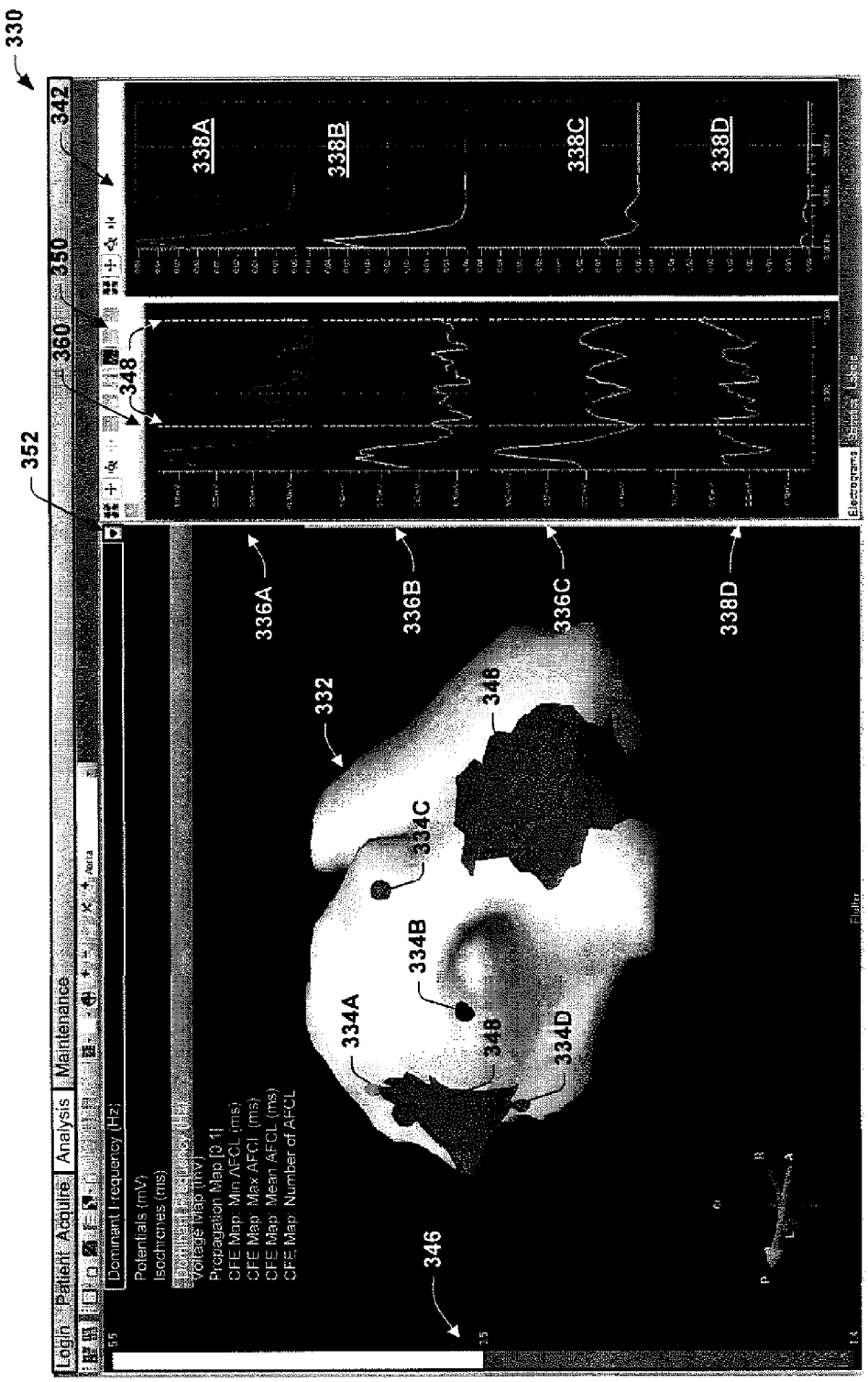
FIG. 13 depicts an example of a graphical user interface demonstrating visualization of frequency information that can be implemented according to an aspect of the invention.

FIG. 13 depicts an example GUI 330 in which mapping controls have been activated to depict a dominant frequency map superimposed on the graphical representation of the patient's heart, indicated at 332. In the example of FIG. 11, four virtual electrodes 334A, 334B, 334C and 334D are positioned at desired locations on a patient's heart. Corresponding electrograms 336A, 336B, 336C and 336D and power spectrum plots 338A, 338B, 338C and 338D are depicted in respective windows 340 and 342.

Additionally in FIG. 13, the dominant frequency map provides spatial information about the dominant frequency over the surface of the heart 332 according to a corresponding to a scale 344, such as can be implemented as a color code or gray scale code. Thus, reference to the scale 344 when viewing the dominant frequency map of the heart 332 demonstrates to the user the dominant frequency for each region of the heart.

The dominant frequency can vary according to the interval for which the dominant frequency is computed. Thus in FIG. 13, caliper user interface elements 348 can be provided in the electrogram window, for example, to enable a user to select or vary a time interval for which the dominant frequency is calculated, such as via a pointer or cursor. The caliper user interface element 348 can be activated for selecting the interval in response to activating a corresponding interval selector user interface element 350, such as a button or other user interface feature.

Also depicted in FIG. 13 is a user interface element (e.g., a drop down context menu) 352 that defines what type of electroanatomic map is superimposed on the heart 332. Thus, in the example of FIG. 13, dominant frequency is selected, resulting in the map shown. It will be appreciated that other types of maps could be selected by a user (via the user interface element 352) for display superimposed on the heart, such as shown and described herein.

In one embodiment of the invention, the dominant frequencies in each electrogram are displayed spatially on the 3D geometry of the heart 332, which may be called a real-time spectral map (RTSM). Each frequency from lowest to highest will be visually identified by a unique colormap. RTSMs from various electrogram segments can be compared visually in separate cardioframes or statistically using measures including difference maps and correlation coefficients. The spatial variability, gradient and dispersion of dominant frequencies in each RTSM can also be computed and, for example, presented as numerical data, queried through the GUI's virtual electrode or presented as a 3D map.

The temporal organization of the dominant frequency in the spectrum, or regularity, can be estimated mathematically, such as by dividing the area under the narrow band of the dominant frequency (+/− band where the power falls <50% of the maximum power at the dominant frequency) and each of its harmonics with the total area within a specified band (e.g., about 5 Hz). Such regularity measures of dominant frequency sites can be identified spatially via observing and querying RTSMs. Thus, the regularity for a given virtual electrode can be computed and provided as a regularity index. A consistency or repeatability index can be derived by comparing RTSMs from contiguous segments.

The dominant frequencies can also be presented as a 3D animation over time, showing consistency and/or distribution of DF sites over segments of analyzed data —Star Spectral map.

Region of Interest Analysis

Another function that can be implemented via an appropriated GUI element is a comparison function, which can be employed to compare the electrical activity spatially and/or temporarily. For example, a user can compare electrical activity for two different spatial locations on the patient's heart for the same heartbeat. Additionally or alternatively, a user can compare electrical activity of the same spatial location for two different heartbeats. As an example a user can compare an arrhythmia beat with a paced beat or an arrhythmia beat with a normal beat, such as for the same spatial location of the patient's heart (e.g., corresponding to a virtual electrode). The results of the comparison can be displayed to a user, such as in the form of a map superimposed on a 3-D representation of the patient's heart similar to the representations shown and described herein. The comparison can be a numerical comparison as well as any statistical type of comparison.

Additionally, as described herein, the systems and methods can be utilized interpretatively, such as during an EP study. For example, a user can compare beats for a given anatomical region of interest before ablation, during an ablation procedure as well as after ablation. The results of such comparisons can be presented as a function of the comparison as a map or as a plurality of displays.

Figure 14:
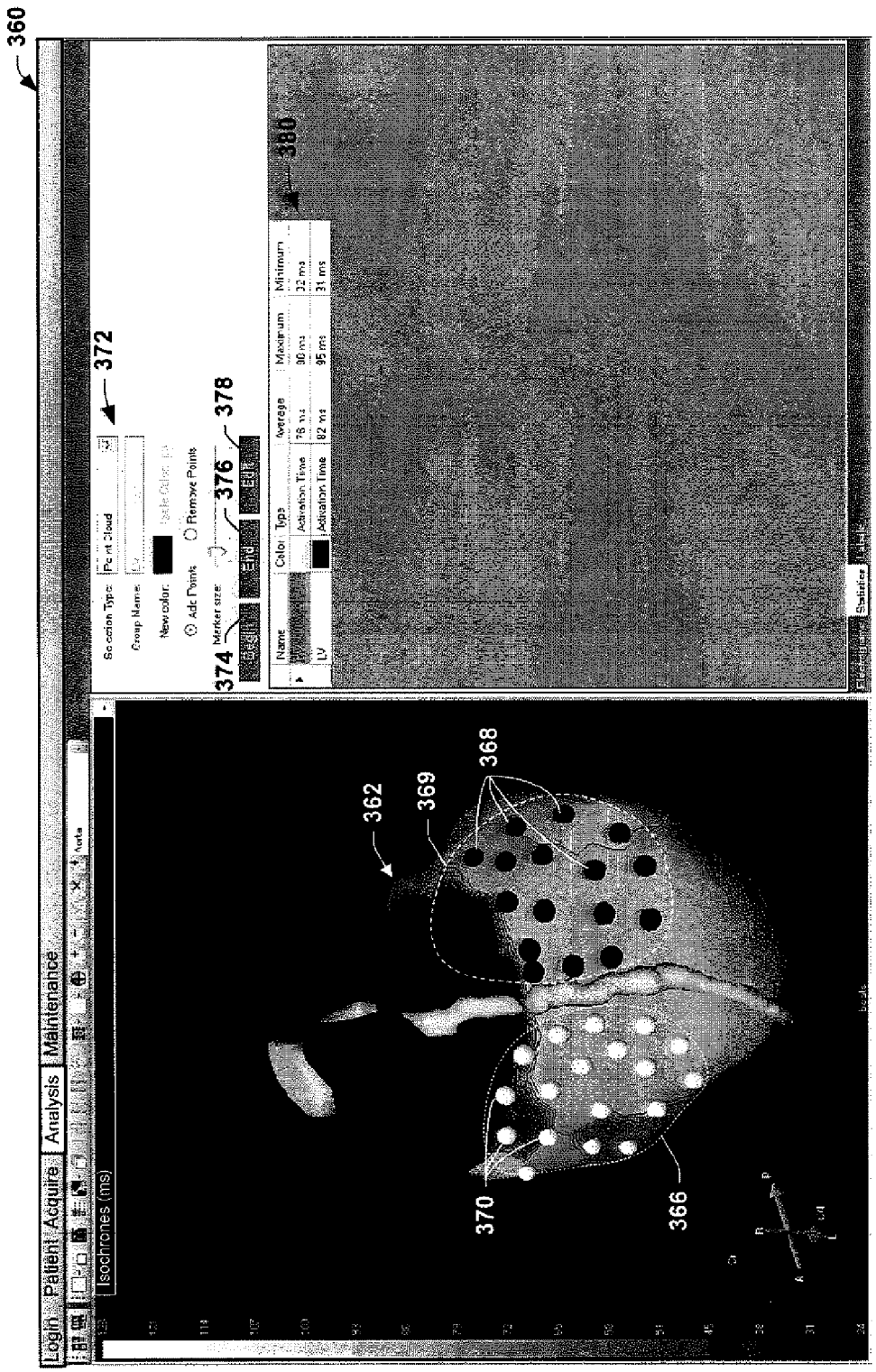
FIG. 14 depicts an example of a graphical user interface demonstrating visualization of region of interest analysis that can be implemented according to an aspect of the invention.

By way of example, FIG. 14 depicts an example GUI 360 in which region of interest analysis has been activated for evaluation of electrophysiology of one or more regions on a surface of a patient's heart 362. In the example of FIG. 14 two regions have been identified for evaluation, indicated by dashed lines 364 and 366. Those skilled in the art will appreciate various methods that can be utilized to select the regions. As one example, a user can position individual virtual electrodes on each region of interest 364 and 366, such as placing electrodes 368 in region 364 and virtual electrodes 370 in region 366. In the illustrated example, the region 364 corresponds to the patient's left ventricle and the region 366 corresponds to the patient's right ventricle.

GUI controls 372 can be provided in an adjacent window, such as to control the color, size and method utilized to mark each region of interest with the virtual electrodes. The GUI controls 372 can also be utilized to selectively remove or edit placement virtual electrodes or portions of each region.

By way of example, a selection mode can be entered for a given region by selecting a begin user interface element (e.g., a button) 374. After placing a desired number of virtual electrodes on the region, a user end the placement mode for that region via another user interface element 376. Another user interface element 378 can be utilized for editing the number or distribution of virtual electrodes for a given region.

Other approaches can be employed to mark a region for analysis. For instance, a user can employ a drawing tool or similar user interface feature to identify each one or more region 364 and 366 on the heart 362. Each identified region can then be automatically populated with an arrangement of virtual electrodes 368 and 370. The number and spatial distribution of electrodes can be programmed by the user. As yet another alternative approach, a list of predefined anatomical landmarks (based on patient geometry data) can be provided to the user for selection. Each selected landmark can be automatically populated with a set of one or more virtual electrodes for analysis.

Once a region 364, 366 has been configured as a virtual electrode structure, electrical information can be displayed in an adjacent display window 380. Information associated with the electrical activity of each region can be provided according to the configuration and placement of virtual electrodes. The information can include statistical information for each region, such as the average, maximum and minimum activation time. A corresponding electroanatomical map can also be superimposed on the surface of the heart 362 (e.g., an isochrone map depicted in the example of FIG. 14). Those skilled in the art will understand and appreciate various other types of information that can be computed and presented to the user based on the arrangement of virtual electrodes 368 and 370, which can include numerical values as well as graphical information.

Morphological Analysis of Electrograms

The relevance of complex fractionated electrograms (CFE) as ablation targets has been clinically observed. These electrograms are found mostly in regions of diseased or infarcted tissue, slow conduction areas or at pivot points where the fibrillatory wavelets turn around at functional or anatomical lines of block. In this subpart of the invention, methods and algorithms are described to identify CFEs and classify them as relevant or transient. A measure of fractionation of the electrogram or Fractionation Index (FI) may be derived by counting the number of transitions in the signal, and combining it with the number of local activations as detected by the multiple activation time detection algorithms elsewhere described in this invention disclosure. A more stringent definition of FI could include amplitude thresholds and cycle lengths obtained from frequency analysis also described elsewhere in this invention disclosure. In one embodiment of the invention, degrees of fractionations can be displayed spatially as 3D complex fractionated electrogram maps (CFEM). Lowest to highest degrees of fractionations can be visually identified by a unique colormap. CFEMs from various electrogram segments can be compared visually in separate cardioframes or statistically analyzed using measures including difference maps and correlation coefficients. The spatial variability of each CFEMs can also be quantified and used to sort out relevant CFE regions as treatment targets.

The shape and morphology of the electrogram can be analyzed and the classified into known or typical morphologies like RS, rS, QRS, qRS, QS, RSR, etc. This classification can be color coded and displayed as a 3D map. Those familiar to EP mapping will recognize that in complex arrhythmias with complex electrogram, this kind of spatial morphology mapping will enable the physician to sort out benign vs. culprit sites, e.g., late activation regions can be excluded and early activation possibilities can be further analyzed.

Cycle Length and Cycle Length Variability (CLV)

As shown and described with respect to FIG. 10, cycle length can be estimated or calculated from multiple activation time methods, such as shown and described herein. As mentioned, the time difference between each pair of contiguous or sequential activations constitutes a corresponding cycle length. A measure of the variability of cycle length within an electrogram and spatially among all or selected electrograms can be quantified to estimate cycle length variability. For instance, reciprocal of the dominant frequency can be used to calculate mean cycle length.

A spatial time-domain approach to determining cycle length is by selecting sites that are representative of cycle length and using that value to derive auto-relation indices with all other spatial electrograms. This could be displayed as a spatial map showing regions that belong to the particular cycle length and sites that are outliers. This process can be repeated for other electrogram-cycle length combinations to quickly estimate regions of variable and outlier cycle length that are of significant in identifying treatment targets.

This cycle length and regions of its variability is presented as a spatial 3D map, the cycle length map (CLM). The variability and dispersion of CL can also be presented as a 3D map.

Figure 15:
FIG. 15 depicts an example of a graphical user interface demonstrating visualization of complex fractionated electrograms that can be implemented according to an aspect of the invention.

By way of example FIG. 15 depicts an example of a GUI 400 in which a CFE map is superimposed on the surface of a graphical representation of a heart model 402. In the example of FIG. 15, the GUI 400 includes a map of minimum activation front cycle length, such as can computed for a plurality of points on the surface of the heart based on multiple activations for each point for a selected interval. In the example of FIG. 15, two virtual electrodes 404 and 406 have been positioned at user-selected locations. Electrograms 410 and 412 are generated in an adjacent window 408 based on electroanatomic data and the location data for each of the virtual electrodes 404 and 406.

A time interval has also been set. Similar to described herein, a button or other user interface element 414 can be utilized by a user to activate an interval selection function. In response to activation of the interval selector, respective calipers 416 and 418 are provided for adjusting the interval. The activation time and, in turn, cycle lengths for each of the plurality of points on the heart can be computed according to the interval. A corresponding static representation of the minimum cycle length for each point on the heart can be represented graphically, such as shown in FIG. 15. A corresponding scale can be provided so that a user can discern what the minimum cycle length is over the surface of the heart 402.

FIG. 15 also depicts amplitude calipers 420 and 422 that can be activated and set to define amplitude range for the map that is being generated. Thus, electrograms that do not fall within the selected range can be excluded from consideration when computing activation times and determining the minimum (or other statistical quantity) from the activation times.

Figure 16:
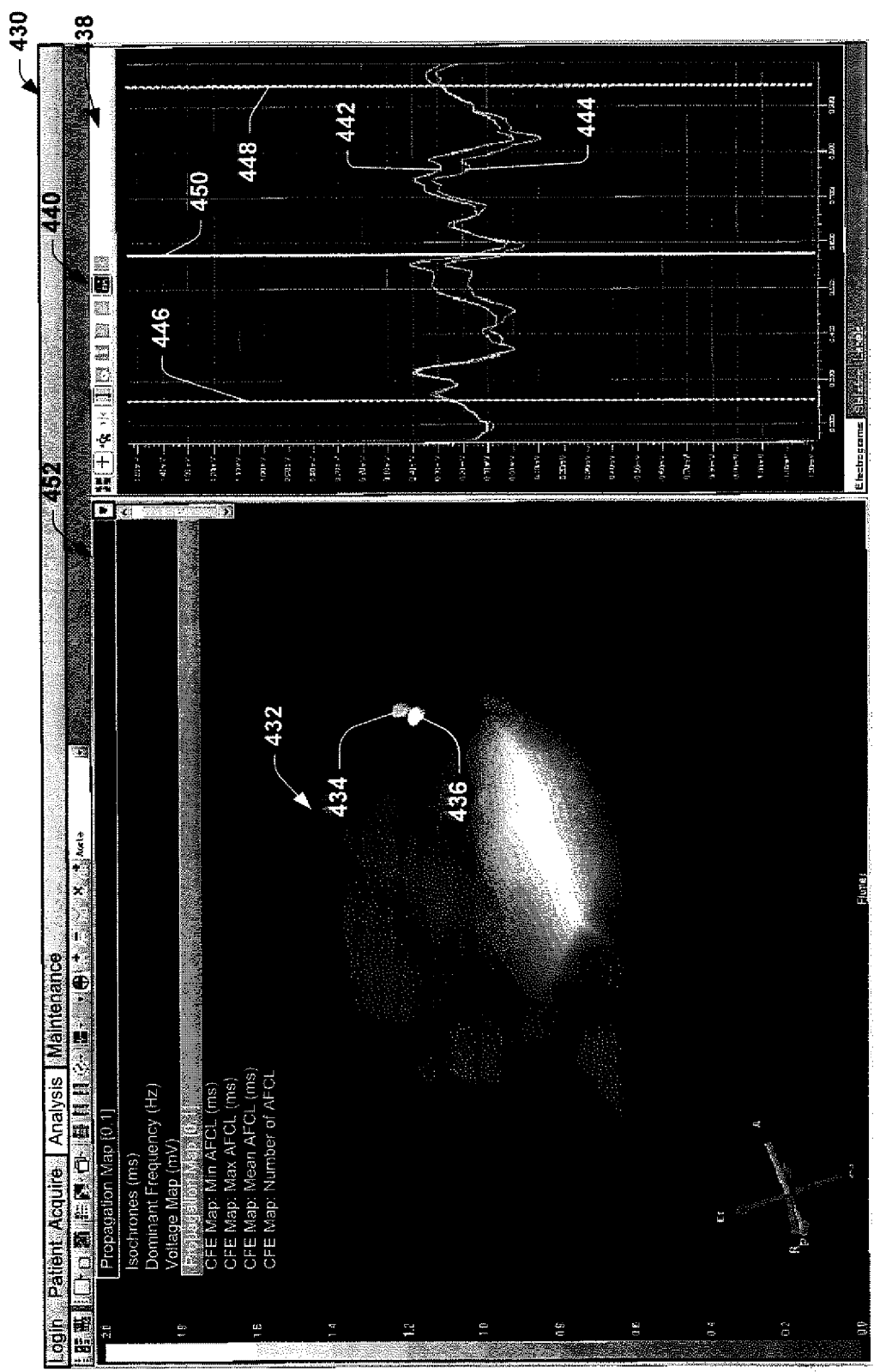
FIG. 16 depicts an example of a graphical user interface demonstrating visualization of propagation of electrical signals that can be implemented according to an aspect of the invention.

FIG. 16 depicts another example of another GUI 430 that can be implemented. In this example, a propagation map superimposed on a 3D representation of a patient's heart is depicted at 432 for a given instance in time. It is to be understood and appreciated that the propagation map (corresponding to propagation of activation times on the epicardial surface of the heart) varies as a function of time according to the electrical activity of the heart. The activation times for a plurality of points on the surface can be computed, such as according to methods shown and described herein. In the example of FIG. 16, two virtual electrodes 434 and 436 are placed at user-selected locations on the graphical representation of the patient's heart 432, responsive to which an adjacent electrogram window 438 displays corresponding electrograms 442 and 444.

An interval selector can be activated by selecting an interval selector user interface element 440. In response to activation of the interval selector, respective calipers 446 and 448 are provided for selectively adjusting the interval. The activation time for each of the plurality of points on the heart can be computed according to the selected interval.

In the example, of FIG. 16, the propagation of the activation front can be dynamically visualized as an animated map. For instance, this dynamic visualization can be visualized and selectively displayed to a user based on the use of a "CINE" caliper function of the available tools. For example, the GUI 430 can include a GUI element that can be selected to present the user with the cursor or caliper 450 that is superimposed on the electrogram window 438 for movement between the interval calipers 446 and 448. IN the example, FIG. 16, the cursor 450 is depicted as a vertical line that is moveable horizontally in the electrogram window 438. The horizontal position of the CINE caliper corresponds to a current time at which activation information is displayed on the map at 432. Those skilled in the art will appreciate that, additionally or alternatively, other means can be provided to identify the current time associated with map being displayed. For example, a clock or counter can be provided to show the elapsed time for the dynamic map. Other graphical elements can also be provided to demonstrate a current place in time for the electrogram for which the corresponding map is being displayed. The CINE cursor 450 thus can traverse between the start and stop time calipers 446 and 448, which can be fixed while the dynamic map is varied over time. The calipers, of course, can be adjusted as shown and described herein, which may be performed manually or automatically.

By way of further example, a user can drag the graphical representation of the cursor 450 to a desired position between the start and stop time intervals 446 and 448, such as by using a mouse or other user input device (e.g., a touch screen). As the CINE cursor is dragged across the electrogram, the corresponding representation of the patient's heart will be modified to display the information in the map frame according to the location of the CINE cursor 250 relative to the electrogram. Additionally or alternatively, a user can employ a corresponding user interface element to cause a CINE cursor 450 to automatically move across the electrogram from the start time across the electrogram to the stop time. As the cursor automatically traverses from the start time to the stop time, the corresponding potential map at 432 will change and reflect the current data according to the time associated with the CINE cursor.

Another workflow tool function can be utilized to set an appropriate user interface element to cause the CINE cursor to 'rock' repeatedly back and forth between the start and end calipers 446 and 448. This back-and-forth movement of the cursor affords a user an opportunity to visualize changes in the potential map that is displayed at 240—both in normal forward time and in a reverse temporal direction.

A user can manually adjust each of the respective start and stop locations 266 and 268 by dragging them to an appropriate location. Alternatively or additionally, the methods described herein can be utilized to automatically select a user defined interval such as corresponding to a given heartbeat, or a type of heartbeat or a set of one or more beats or a period that is centered about a given type of electro activity.

Organization Index (OI)

During an Afib ablation procedure, chaotic rhythms often organize themselves into more organized rhythms including flutter and tachycardia. An organization index can be derived by measuring the periodicity of electrograms over the entire heart for each real time electrogram segment. An OI of 1 indicates highly periodic activity like macro-reentrant flutter. Regions of uniform cycle length in an interval will be displayed as highly organized regions. An OI indicator in the GUI will be very useful in quantifying the number of times and what points the rhythm became organized during the procedure.

Paced Mapping

As a special case, the analysis techniques described in 1-4 can be used in the context of paced mapping. Paced mapping involves stimulating different sites on the heart to elicit a 'paced beats'. Pacing can be performed at sites identified by the aforementioned techniques. The resulting paced beats can be analyzed and presented using the same techniques described for complex electrical activity. The resultant maps can be presented in cardioframes alongside intrinsic electrical activity maps and also queried and compared. Maps for intrinsic activity and paced activity can be compared spatially either visually or using mathematical measures like correlation coefficients also displayed as a 3D spatial map.

Repolarization Mapping

The recovery of the each region of the heart following activation can be analyzed to understand the recovery of the heart. Unlike activation, recovery of the heart is a property of each cardiac cell. Disease alters the properties of the cells, thereby altering global repolarization. Also, a chamber that has been in chaotic activity for a period of time starts to develop changes in its recovery. Mapping regional recovery properties has the potential to identify regions that may be instrumental in maintaining and sustaining fibrillatory conduction.

Spatial recovery times can be estimated from the recovery component of each spatial electrogram (e.g., the T-wave) by calculating its first time derivative. The difference between this recovery time and the activation time (previously described in the application) can be calculated for each spatial electrogram to give an estimated of the spatial Activation Recovery Interval (ARI) that represents local recovery/repolarization properties. The ARI can be computed for each of the plurality points on the surface of the heart for which electroanatomic data (e.g., corresponding to electrograms) is available. This ARI can be displayed in the form of a spatial 3D map on the surface of the heart similar to other maps shown and described herein.

ARIs can be compared between anatomical regions of the heart to derive spatial estimates of the dispersion of ARIs (an indicator of underlying disease). For example, a user can select two or more virtual electrodes at points on the heart. The difference between ARIs for each pair of virtual electrode locations provides an indication of the dispersion for the virtual electrode pair.

Example Operating Environment

FIG. 18 illustrates one example of a computer system 500 of the type that can be utilized to implement one or more embodiments of the systems and methods described herein for visualizing physiological data relating to a patient's organ. The computer system 500 can be implemented on one or more general purpose networked computer systems, embedded computer systems, routers, switches, server devices, client devices, various intermediate devices/nodes and/or stand alone computer systems. Additionally, the computer system 500 or portions thereof can be implemented on various mobile or portable clients such as, for example, a laptop or notebook computer, a personal digital assistant (PDA), and the like.

The system bus 508 may be any of several types of bus structure including a memory bus or memory controller, a peripheral bus, and a local bus using any of a variety of conventional bus architectures such as PCI, VESA, Microchannel, ISA, and EISA, to name a few. The system memory 506 includes read only memory (ROM) 510 and random access memory (RAM) 512. A basic input/output system (BIOS), containing the basic routines that help to transfer information between elements within the computer 502, such as during start-up, is stored in ROM 510.

The computer 502 also may include, for example, a hard disk drive 514, a magnetic disk drive 516, e.g., to read from or write to a removable disk 518, and an optical disk drive 520, e.g., for reading from or writing to a CD-ROM disk 522 or other optical media. The hard disk drive 514, magnetic disk drive 516, and optical disk drive 520 are connected to the system bus 508 by a hard disk drive interface 524, a magnetic disk drive interface 526, and an optical disk drive interface 528, respectively. The drives and their associated computer-readable media provide nonvolatile storage of data, data structures, computer-executable instructions, etc. for the computer 502. Although the description of computer-readable media above refers to a hard disk, a removable magnetic disk and a CD, it should be appreciated by those skilled in the art that other types of media which are readable by a computer, such as magnetic cassettes, flash memory cards, digital video disks, Bernoulli cartridges, and the like, may also be used in the exemplary operating environment 500, and further that any such media may contain computer-executable instructions for performing the methods of the present invention.

A number of program modules may be stored in the drives and RAM 512, including an operating system 530, one or more application programs 532, other program modules 534, and program data 536. The operating system 530 in the computer 502 could be any suitable operating system or combinations of operating systems. The application programs 516, other program modules 517, and program data 518 can cooperate to provide a visualization of output results for a patient's organ, such as shown and described herein.

A user may enter commands and information into the computer 502 through one or more user input devices, such as a keyboard 538 and a pointing device (e.g., a mouse 540). Other input devices (not shown) may include a microphone, a joystick, a game pad, a satellite dish, a scanner, or the like. These and other input devices are often connected to the processing unit 504 through a serial port interface 542 that is coupled to the system bus 508, but may be connected by other interfaces, such as a parallel port, a game port or a universal serial bus (USB). A monitor 544 or other type of display device is also connected to the system bus 508 via an interface, such as a video adapter 546. In addition to the monitor 544, the computer 502 may include other peripheral output devices (not shown), such as speakers, printers, etc. Thus, the output representation for a virtual electrode is not limited to a graphical representation on a display.

The computer 502 may operate in a networked environment using logical connections to one or more remote computers 560. The remote computer 560 may be a workstation, a server computer, a router, a peer device, or other common network node, and typically includes many or all of the elements described relative to the computer 502, although, for purposes of brevity, only a memory storage device 562 is illustrated in FIG. 15. The logical connections depicted in FIG. 15 may include a local area network (LAN) 564 and a wide area network (WAN) 566. Such networking environments are commonplace in offices, enterprise-wide computer networks, intranets, and the Internet.

When used in a LAN networking environment, the computer 502 is connected to the local network 564 through a network interface or adapter 568. When used in a WAN networking environment, the computer 502 typically includes a modem 570, or is connected to a communications server on an associated LAN, or has other means for establishing communications over the WAN 566, such as the Internet. The modem 570, which may be internal or external, is connected to the system bus 508 via the serial port interface 542. In a networked environment, program modules depicted relative to the computer 502, or portions thereof, may be stored in the remote memory storage device 562. It will be appreciated that the network connections shown are exemplary and other means of establishing a communications link between the computers 502 and 560 may be used.

In accordance with the practices of persons skilled in the art of computer programming, the present invention has been described with reference to acts and symbolic representations of operations that are performed by a computer, such as the computer 502 or remote computer 560, unless otherwise indicated. Such acts and operations are sometimes referred to as being computer-executed. It will be appreciated that the acts and symbolically represented operations include the manipulation by the processing unit 504 of electrical signals representing data bits which causes a resulting transformation or reduction of the electrical signal representation, and the maintenance of data bits at memory locations in the memory system (including the system memory 506, hard drive 514, floppy disks 518, CD-ROM 522, and shared storage system 510) to thereby reconfigure or otherwise alter the computer system's operation, as well as other processing of signals. The memory locations where such data bits are maintained are physical locations that have particular electrical, magnetic, or optical properties corresponding to the data bits.

In view of the features shown and described herein, those skilled in the art will understand and appreciated various modifications and implementations of spatial visualizations that can be utilized. As an example, a user can select a variety of other functions via corresponding user interface elements that can be provided on a cardioframe. For instance, a user can isolate one or more beats from one or more electrograms. The isolation of heartbeats can be a manual procedure, such as by using calipers similar to those shown and described herein. Alternatively or additional, the identification and isolation of a given heartbeat can be automated by performing corresponding methods.

Additionally, in one embodiment, data is acquired concurrently as epicardial data for the entire heart. As a result of acquiring data in this manner, the representation of the data being presented (e.g., in a cardioframe) can correspond to electrical activity for a single chamber, for two chambers, for three chambers or for all four chambers of the patient's heart. Since the data is acquired concurrently for all chambers, a user can employ methods shown and described herein to perform comparisons on any number of chambers. Such comparisons can include temporal comparisons for multiple heart chambers for an isolated beat of interest. The visual representation further can provide comparisons for selected chambers of the patient's heart which can further be presented to the user.

As a further example, the methods can be utilized to calculate minimum or maximum activation times for each of one or more intervals of interest. Methods can also be utilized to compute standard deviations, statistics across the one or more intervals that have been selected.

The approach described herein further can facilitate pattern matching. For example, pattern matching methods can be employed to determine (to a degree of statistical likelihood) the repeatability of patterns. Thus patterns can be detected and analyzed further based upon the methods shown and described herein. The pattern matching can be utilized in the frequency domain spectrum or in the time domain spectrum.

One further functionality that can be associated with the cardioframe and, in particular, with the isochrone maps, is to identify a 'line of block.' The line of block can be computed, for example, based on the gradient calculated for a given isochrones map. Methods can thus be utilized to analyze the gradient of the isochrones map as well as to compute maximum conduction velocities. Based on further analysis of the gradient over a plurality of heart beats, it can be determined whether the line of block corresponds to a functional condition associated with the heart, which changes beat to beat and then usually not repeatable. It can also be determined from such analysis whether such line of block might correspond to an anatomical condition, such as may be due to a structural defect since the line of block may be repeatable for a given region of the patient's heart.

What have been described above are examples and embodiments of the invention. It is, of course, not possible to describe every conceivable combination of components or methodologies for purposes of describing the invention, but one of ordinary skill in the art will recognize that many further combinations and permutations of the invention are possible. Accordingly, the invention is intended to embrace all such alterations, modifications and variations that fall within the scope of the appended claims. In the claims, unless otherwise indicated, the article "a" is to refer to "one or more than one."

What is claimed is:

1. A computer implemented method, comprising:
storing electroanatomic data in memory, the electroanatomic data representing electrical activity for an anatomic region within a patient's body;
selecting a time interval for the electrical activity in response to a user selection, wherein the user selection specifies the interval based on interacting with a representation of a waveform of electrical activity for a given location of a plurality of locations for the anatomic region; and
responsive to the user selection of the time interval, automatically generating a visual representation of physiological information for the user selected time interval by applying at least one analysis method to the electroanatomic data for each of the plurality of locations of the anatomic region within the user selected interval, the visual representation of physiological information for the user selected time interval being spatially represented on a graphical representation of at least a portion of the anatomic region.

2. The method of claim 1, further comprising:
receiving a user input that modifies the user selected interval;
re-applying the at least one method to the electroanatomic data for each of the plurality of locations of the anatomic region to compute the at least one analysis method for each of a plurality of points across the anatomic region according to the modified user selected interval; and
dynamically modifying the visual representation based on the re-application of the at least one analysis method to the electroanatomic data for each of the plurality of locations of the anatomic region within the modified user selected interval.

3. The method of claim 2, wherein a plurality of activation times are computed for each of the plurality of points, the method further comprising:
determining a cycle length between sequential activation times for each of the plurality of points; and
generating the visual representation as spatial map indicative of at least one of cycle length and a number activation times for each of the plurality of points.

4. The method of claim 2, further comprising setting a user-defined cycle length in response to a user input; and
generating the visual representation as a map superimposed on the predetermined region based on an autocorrelation of the user-defined cycle length and the activation times computed for each the plurality of points.

5. The method of claim 1, wherein the at least one analysis method is programmed to analyze frequency for a plurality of points on the predetermined anatomic region within the patient's body by computing a frequency spectrum for each the plurality of points according to the user selected interval.

6. The method of claim 1, further comprising:
   determining a dominant frequency in the frequency spectrum for each the plurality of points; and
   generating the visualization to include a dominant frequency map on the graphical representation of the anatomic region.

7. The method of claim 1, further comprising selecting the at least one analysis method from a plurality of preprogrammed analysis methods in response to a user selection input, the plurality of preprogrammed methods comprising instructions programmed to determine at least two of activation time, frequency spectrum information, dominant frequency, voltage potential, and electrogram fractionation.

8. A computer implemented method, comprising:
   storing electroanatomic data in memory, the electroanatomic data representing electrical activity for an anatomic region within a patient's body:,
   receiving a user input that defines location data corresponding to a user-selected location for at least one virtual electrode on a graphical representation of the anatomic region within the patient's body;
   generating a corresponding waveform of electrical activity for each virtual electrode based on the location data and the electroanatomic data for the received user input;
   selecting a time interval for the electrical activity in response to a user input, wherein the user input specifies the interval based on interacting with the corresponding waveform of electrical activity for the at least one virtual electrode; and
   responsive to the user selection of the time interval, generating a visual representation of physiological information for the user selected time interval by applying at least one analysis method to the electroanatomic data for the anatomic region, the visual representation being spatially represented on a graphical representation of at least a portion of the anatomic region.

9. The method of claim 8, wherein the visual representation comprises a graphical representation of an electroanatomic map, the method further comprising superimposing a graphical representation of the at least one virtual electrode on the interactive graphical representation of the anatomic region within the patient's body in response to the receiving of the user input.

10. The method of claim 1, wherein the user selected interval defines a start time and an end time that span the time interval, the method further comprising dynamically modifying the visual representation in an animated manner to represent temporal changes in the physiological information within the time interval spatially depicted by the graphical representation of the anatomic region within the patient's body.

11. The method of claim 10, further comprising generating an indication of a current time in the interval corresponding to the dynamically modified the visual representation.

12. The method of claim 11, wherein the interval is selected from an interactive graphical representation of temporal electrophysiology information for at least one point on the anatomic region within the patient's body, the method further comprising repeatedly traversing the interval between the start time and the stop time and dynamically modifying the visual representation based on data associated with a current time during each traversal of the interval.

13. The method of claim 1, further comprising applying an inverse method to compute the electroanatomical data for the anatomic region within the patient's body based on patient electrical data acquired for the patient via non-invasive body surface electrodes and geometry data.

14. The method of claim 13, wherein the geometry data comprises at least one of a generic representation of the anatomic region within the patient's body or a patient-specific representation of the anatomic region within the patient's body derived from imaging data for the patient.

15. The method of claim 1, further comprising:
   preprocessing electrical data acquired from a patient, the preprocessing including selecting at least one sample interval for the acquired electrical data in response to a user input, the electroanatomic data being generated from the acquired electrical data for the selected at least one sample interval, and
   wherein the selected interval is an analysis interval, the electroanatomic data being generated according to the electrical data acquired for the at least one sample interval, the visual representation of physiological information for the user selected interval being generated by applying the at least one analysis method to the electroanatomic data that is generated according to the at least one sample interval, such that the visual representation is variable and responsive to modifications in the analysis interval based on the user selection thereof, while the at least one sample interval remains fixed.

16. The method of claim 15, wherein the at least one sample interval comprises multiple non-temporally contiguous sample intervals, the method further comprising aggregating the acquired electrical data for each of the multiple non-temporally contiguous sample intervals to provide a spliced set of electrical data, the electroanatomic data being generated based on the spliced set of electrical data.

17. A non-transitory computer readable medium having instructions for performing a method comprising:
   preprocessing electrical data acquired from a patient, the preprocessing including selecting at least one sample interval for the acquired electrical data in response to a user input;
   generating electroanatomic data for an anatomic region of interest based on the acquired electrical data for the selected at least one sample interval;
   storing the electroanatomic data for an anatomic region of interest;
   selecting an analysis time interval for the electrical activity in response to a user selection, wherein the user selection specifies the analysis time interval based on interacting with a representation of a waveform of electrical activity for a given location of the anatomic region;
   selecting at least one analysis method in response to a user input; and
   generating a visual representation of physiological information for the analysis time interval by applying the selected at least one analysis method to the electroanatomic data that is generated according to the selected at least one sample interval, such that the visual representation is variable and responsive to modifications in the analysis interval based on the user selection thereof, while the at least one sample interval remains fixed, the visual representation being spatially represented on a graphical representation of at least a portion of the anatomic region of interest.

18. The medium of claim 17, wherein the method further comprises applying an inverse method to compute the electroanatomical data for the anatomic region of interest based on the acquired electrical data for at least the selected at least one sample interval, the acquired electrical data being acquired for the patient via non-invasive body surface electrodes and geometry data, the geometry data corresponding to at least one of geometry of anatomy of the patient or mathematical model.

19. The medium of claim 17, wherein the at least one analysis method is selected from a set of preprogrammed analysis methods or is programmed in response to a user input.

20. The method of claim 1, wherein the at least one method is programmed to dynamically identify one or more anatomical locations that meet user-defined criteria and to automatically generate the visual representation to include a virtual identifier at each location of the anatomic region that satisfies the user-defined criteria.

* * * * *